(12) United States Patent
Koizumi et al.

(10) Patent No.: US 10,074,803 B2
(45) Date of Patent: Sep. 11, 2018

(54) COMPOSITION, LAMINATE, METHOD OF MANUFACTURING LAMINATE, TRANSISTOR, AND METHOD OF MANUFACTURING TRANSISTOR

(71) Applicant: NIKON CORPORATION, Tokyo (JP)

(72) Inventors: Shohei Koizumi, Atsugi (JP); Takashi Sugizaki, Yokohama (JP); Kenji Miyamoto, Yokohama (JP); Yusuke Kawakami, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 15/495,360

(22) Filed: Apr. 24, 2017

(65) Prior Publication Data

US 2017/0229653 A1 Aug. 10, 2017

Related U.S. Application Data

(60) Division of application No. 14/733,214, filed on Jun. 8, 2015, now abandoned, and a continuation of
(Continued)

(30) Foreign Application Priority Data

Dec. 12, 2012 (JP) ................... 2012-271761
Jun. 3, 2013 (JP) ................... 2013-116617

(51) Int. Cl.
| | |
|---|---|
| *C08F 2/46* | (2006.01) |
| *C08G 61/04* | (2006.01) |
| *H01L 51/00* | (2006.01) |
| *H01L 51/05* | (2006.01) |
| *H01L 51/10* | (2006.01) |

(Continued)

(52) U.S. Cl.
CPC .......... *H01L 51/0035* (2013.01); *B32B 27/16* (2013.01); *C08G 59/245* (2013.01); *C08G 59/32* (2013.01); *C08G 59/3245* (2013.01); *C08G 59/4064* (2013.01); *C08G 59/66* (2013.01); *C09D 5/24* (2013.01); *C09D 163/00* (2013.01); *H01L 51/0023* (2013.01); *H01L 51/0043* (2013.01); *H01L 51/0097* (2013.01); *H01L 51/052* (2013.01); *H01L 51/055* (2013.01); *H01L 51/0545* (2013.01); *H01L 51/105* (2013.01); *B32B 2307/202* (2013.01); *B32B 2307/206* (2013.01)

(58) Field of Classification Search
CPC .. C09D 5/24; C08G 59/3245; C08G 59/4064; C08G 59/245; C08G 59/66; C08G 59/32; H01L 51/0035; H01L 51/105; H01L 51/0097; H01L 51/055; H01L 51/043; H01L 51/0545; H01L 51/0023; H01L 51/052; B32B 2307/202; B32B 2307/206; B32B 27/16

USPC ................................... 522/1; 520/1
See application file for complete search history.

(56) References Cited

U.S. PATENT DOCUMENTS

| | | | |
|---|---|---|---|
| 4,339,567 A | | 7/1982 | Green et al. |
| 5,730,764 A | | 3/1998 | Williamson |

(Continued)

FOREIGN PATENT DOCUMENTS

| | | | |
|---|---|---|---|
| CN | 101973966 | * | 7/2012 |
| EP | 0 507 271 A2 | | 10/1992 |

(Continued)

OTHER PUBLICATIONS

Cheng et al, CN 101973966 Machine Translation, Jul. 4, 2012 (Year: 2012).*

(Continued)

*Primary Examiner* — Jessica Whiteley

(57) ABSTRACT

Laminate, method of manufacturing laminate, transistor, and method of manufacturing transistor using a composition having the following (a) to (c):
(a) a first organic compound represented by Formula (1) below (R represents a hydrogen atom or a glycidyl group. A plurality of Rs may be identical to or different from each other, but each of at least two Rs is a glycidyl group),
(b) a second organic compound represented by Formula (2) below, and
(c) a photocationic polymerization initiator

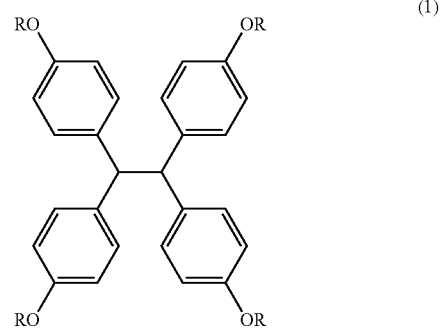

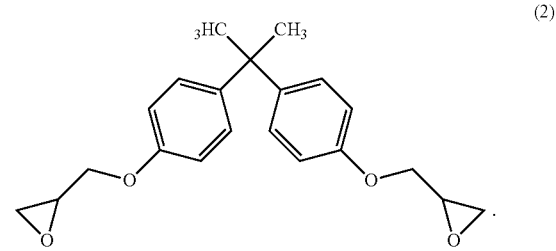

14 Claims, 26 Drawing Sheets

Related U.S. Application Data application No. PCT/JP2013/082843, filed on Dec. 6, 2013.

(51) Int. Cl.
| | |
|---|---|
| C08G 59/24 | (2006.01) |
| C08G 59/32 | (2006.01) |
| C08G 59/66 | (2006.01) |
| C08G 59/40 | (2006.01) |
| C09D 5/24 | (2006.01) |
| C09D 163/00 | (2006.01) |
| B32B 27/16 | (2006.01) |

(56) References Cited

U.S. PATENT DOCUMENTS

| | | | |
|---|---|---|---|
| 5,946,551 | A | 8/1999 | Dimitrakopoulos et al. |
| 6,077,891 | A | 6/2000 | Herbst |
| 6,232,157 | B1 | 5/2001 | Dodabalapur et al. |
| 2004/0077821 | A1 | 4/2004 | Hwang et al. |
| 2005/0279995 | A1 | 12/2005 | Shin et al. |
| 2008/0166550 | A1 | 7/2008 | Inoue |
| 2009/0206328 | A1* | 8/2009 | Matsukawa ........... G03F 7/0007 257/40 |
| 2010/0056725 | A1 | 3/2010 | Larson |
| 2010/0164368 | A1 | 7/2010 | Kong |

FOREIGN PATENT DOCUMENTS

| | | | |
|---|---|---|---|
| JP | 56-149402 | | 11/1981 |
| JP | 5-9269 | | 1/1993 |
| JP | 6-233486 | | 8/1994 |
| JP | 2004-143444 | | 5/2004 |
| JP | 2006-28497 | | 2/2006 |
| JP | 2010-254757 | | 11/2010 |
| WO | WO-2013176247 A1 * | 11/2013 | ......... C23C 18/1651 |

OTHER PUBLICATIONS

Kawakami et al, WO 2013176247 Machine Translation, May 24, 2013 (Year: 2013).*
Kaji, Molecular Design of Epoxy Resins for Microelectronics Packaging, May 5, 1995, American Chemical Society, pp. 220-233 (Year: 1995).*
PCT International Search Report dated Mar. 11, 2014 in corresponding International Patent Application No. PCT/JP2013/082843.
Written Opinion of the International Searching Authority dated Mar. 11, 2014 in corresponding International Patent Application No. PCT/JP2013/082843.
Kaji, Molecular design of epoxy resins for microelectronics packaging, American Chemical Society, May 5, 1995, pp. 220-233.
Office Action dated Oct. 25, 2016 in U.S. Appl. No. 14/733,214.
Office Action dated Jul. 25, 2016 in U.S. Appl. No. 14/733,214.
Japanese Notice of Reasons for Rejection dated Oct. 10, 2017 in corresponding Japanese Patent Application No. 2014-552021.

* cited by examiner

[FIG. 15]

FIG. 16
(a) RAW MATERIAL SOLUTION 1
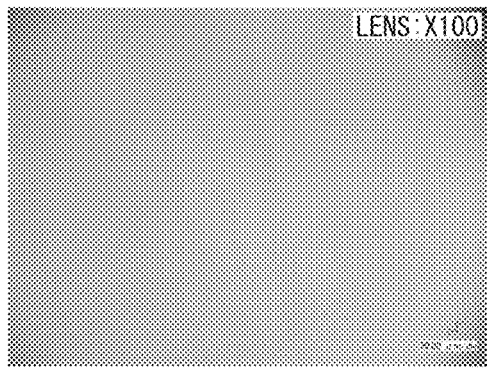
COATING UNEVENNESS: NO
(b) RAW MATERIAL SOLUTION 2
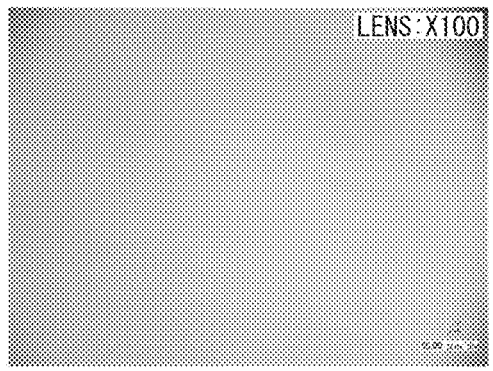
COATING UNEVENNESS: NO
(c) RAW MATERIAL SOLUTION 3
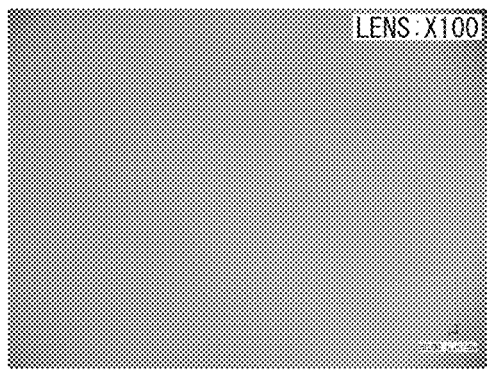
COATING UNEVENNESS: NO
(d) RAW MATERIAL SOLUTION 4
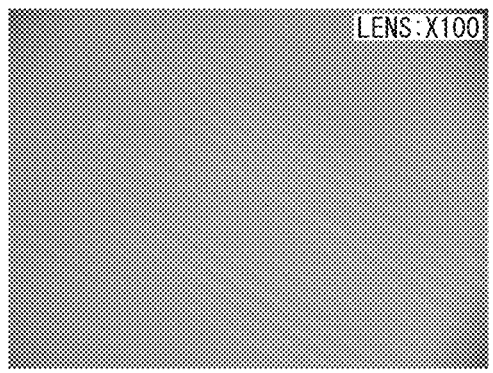
COATING UNEVENNESS: YES
(e) RAW MATERIAL SOLUTION 5
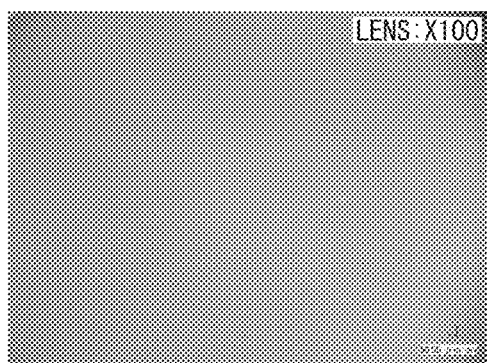
COATING UNEVENNESS: NO
(f) RAW MATERIAL SOLUTION 6
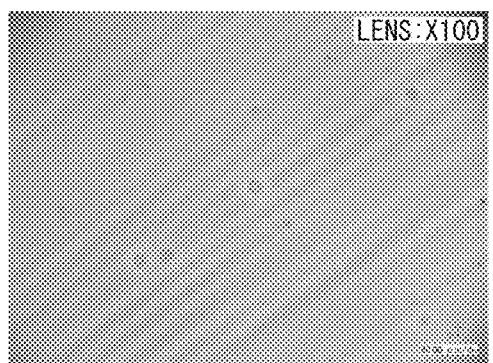
COATING UNEVENNESS: YES FIG. 21
(a)
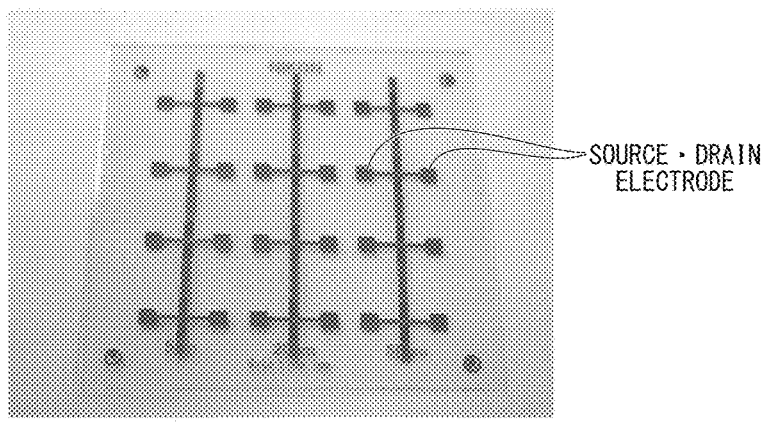
SOURCE · DRAIN ELECTRODE
(b) RAW MATERIAL SOLUTION 2
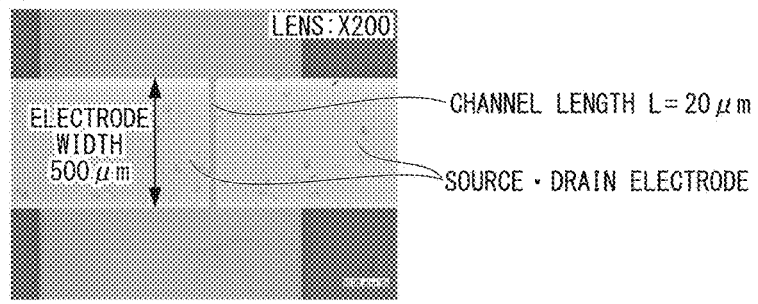
CHANNEL LENGTH L = 20 μm
SOURCE · DRAIN ELECTRODE
ELECTRODE WIDTH 500 μm
(c) RAW MATERIAL SOLUTION 3
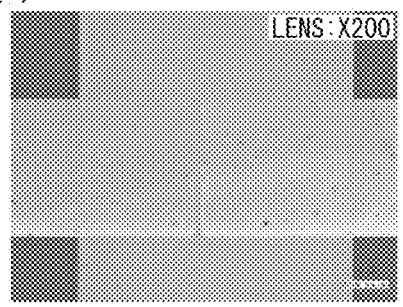
(d) RAW MATERIAL SOLUTION 4
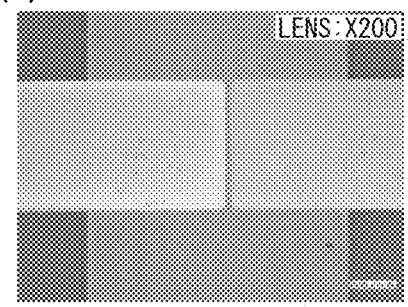
(e) RAW MATERIAL SOLUTION 5
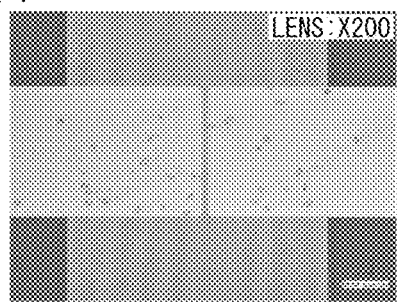
(f) RAW MATERIAL SOLUTION 6
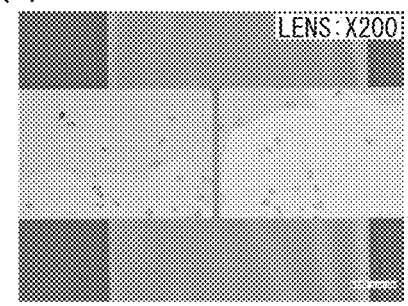

COMPOSITION, LAMINATE, METHOD OF MANUFACTURING LAMINATE, TRANSISTOR, AND METHOD OF MANUFACTURING TRANSISTOR

CROSS-REFERENCE TO RELATED APPLICATIONS

This application is a divisional of U.S. application Ser. No. 14/733,214, filed Jun. 8, 2015, which is a Continuation Application of International Application No. PCT/JP2013/082843, filed on Dec. 6, 2013, which claims priority on Japanese Patent Application No. 2012-271761, filed on Dec. 12, 2012 and Japanese Patent Application No. 2013-116617, filed on Jun. 3, 2013. The contents of the aforementioned applications are incorporated herein by reference.

BACKGROUND

Field

The present invention relates to a composition, a laminate, a method of manufacturing a laminate, a transistor, and a method of manufacturing a transistor.

Related Art

In the related art, a laminate of a conductive layer and an insulator layer has been used in various electronic circuits.

The laminate having such a laminated structure is used, for example, to achieve the miniaturization and high integration of electronic circuits. Specifically, this laminate is used for a printed circuit board, a condenser, a transistor, and the like, each having a multilayer wiring structure.

When forming the above laminate, wirings (conductive layers) to be laminated are insulated from each other by an insulator layer. As the insulator layer, any of an inorganic insulator and an organic insulator may be used (for example, refer to U.S. Pat. No. 5,946,551 and U.S. Pat. No. 6,232,157). Among these, the laminate using an organic insulator is advantageous compared to a laminate using a conventional insulator layer using $SiO_2$ as a formation material in that an insulator layer can be formed in a liquid phase and in that a laminated structure can be formed at a lower temperature without requiring a vacuum process.

In the laminate in which an organic insulator is used in an insulator layer, there is proposed a technology of patterning an insulator layer through a photoresist-free simple method by the combination of polyvinyl phenol (PVP) and an epoxy group-containing compound with a photopolymerization initiator (for example, refer to Japanese Unexamined Patent Application, First Publication No. 2006-28497).

SUMMARY

In recent years, for example, an organic insulator having both excellent insulation properties and excellent dielectric properties, which can be suitably used in a gate insulating film (insulator layer) of a transistor, has been required. Since the conventional organic insulator does not have satisfactory physical properties, additional improvements have been required.

Some aspects of the present invention intend to provide a composition capable of forming an insulator having both excellent insulation properties and excellent dielectric properties. Other aspects of the present invention intend to provide a method of manufacturing a laminate using the composition, a laminate manufactured by the method, a method of manufacturing a transistor, and a transistor manufactured by the method.

A composition according to an aspect of the present invention includes: (a) a first organic compound represented by Formula (1) below; (b) a second organic compound represented by Formula (2) below; and (c) a photocationic polymerization initiator.

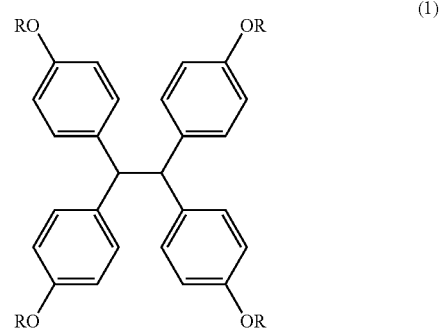

(R represents a hydrogen atom or a glycidyl group. A plurality of Rs may be identical to or different from each other, but each of at least two Rs is a glycidyl group.)

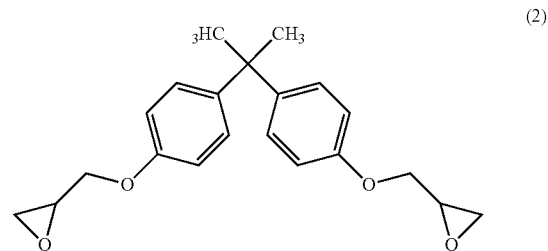

A method of manufacturing a laminate according to another aspect of the present invention includes: applying a solution containing the above-mentioned composition over a conductive layer to form a coating film; and irradiating the coating film with light containing light having an absorption wavelength of the photocationic polymerization initiator contained in the coating film to form an insulator layer.

A laminate according to another aspect of the present invention includes: a conductive layer; and an insulator layer formed by cationic-polymerization of the above-mentioned composition.

A method of manufacturing a transistor according to another aspect of the present invention includes: forming a gate electrode on a substrate; applying a solution containing the above-mentioned composition over the gate electrode to form a coating film; irradiating the coating film with light containing light having an absorption wavelength of the photocationic polymerization initiator contained in the coating film to form a latent image in the light-irradiated region of the coating film; developing the coating film to form an insulator layer; and forming a source electrode and a drain electrode on the surface of a layer including the insulator layer.

A transistor according to another aspect of the present invention includes: a source electrode and a drain electrode; a gate electrode provided corresponding to a channel between the source electrode and the drain electrode; a semiconductor layer provided in contact with the source electrode and the drain electrode; and an insulator layer disposed between the source electrode and the gate electrode and between the drain electrode and the gate electrode, wherein the insulator layer is formed by cationic-polymerization of the above-mentioned composition.

According to some aspects of the present invention, it is possible to provide a composition capable of forming an insulator having both excellent insulation properties and excellent dielectric properties. According to other aspects of the present invention, it is possible to provide a method of manufacturing a laminate using the composition, a laminate manufactured by the method, a method of manufacturing a transistor, and a transistor manufactured by the method.

BRIEF DESCRIPTION OF THE DRAWINGS

FIG. 16 shows photographs showing the results of Example 2.

FIG. 21 shows photographs showing the results of Example 3.

DESCRIPTION OF THE EMBODIMENTS

First Embodiment

Figure 1A:
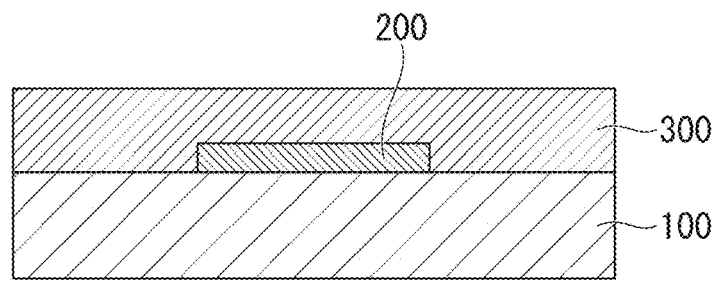
FIG. 1A is a process view showing a method of manufacturing a laminate according to a first embodiment.

Hereinafter, a first embodiment of the present invention will be described.

(Composition)

The composition of the present embodiment is a curable composition including the following (a) to (d):

(a) a first organic compound represented by Formula (1) below;

(b) a second organic compound represented by Formula (2) below;

(c) a photocationic polymerization initiator; and (d) polyvinyl phenol.

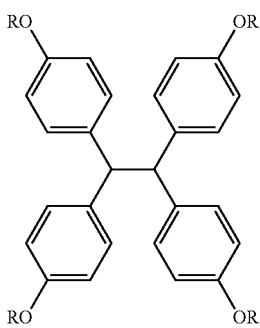

(1)

(R represents a hydrogen atom or a glycidyl group. A plurality of Rs may be identical to or different from each other, but each of at least two Rs is a glycidyl group.)

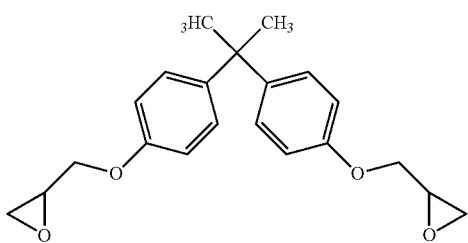

(2)

Hereinafter, there will be described a case that the composition is a curable composition, but the composition of the present invention is not limited to the curable composition.

As the first organic compound (a), an organic compound having 3 or more Rs of a glycidyl group can be used, and an organic compound having all Rs of a glycidyl group is preferable. A specific example of the first organic compound may include tetraphenylol ethane glycidyl ether (412961, manufactured by Sigma-Aldrich Corporation).

A specific example of the second organic compound (b) may include a bisphenol A epoxy monomer (RE310S, manufactured by Nippon Kayaku Co., Ltd.).

The photocationic polymerization initiator (c) is a compound that initiates the cationic polymerization reaction of a curable composition using the cationic species or Lewis acid generated by the absorption of light (for example, ultraviolet light) energy. As the photocationic polymerization initiator, known photocationic polymerization initiators, such as aromatic diazonium salts, aromatic sulfonium salts, aromatic iodonium salts, metallocene compounds, phosphonium salts, and silanol-aluminum complexes, can be used. These compounds may be used alone or in a mixture of two or more.

A specific example of the photocationic polymerization initiator (c) may include OMPH076 manufactured by Glest Inc., which is an aromatic sulfonium salt.

Here, in order to increase the reactivity of the photocationic polymerization initiator (c), a photosensitizer that accelerates the reaction of the photocationic polymerization initiator (c) by absorbing light and transferring the absorbed energy to the photocationic polymerization initiator (c) may be added to the curable composition.

The polyvinyl phenol (d) has a weight average molecular weight of 1000 to 100000, preferably 5000 to 50000, and more preferably 10000 to 30000. Specifically, polyvinyl phenol (436224, manufactured by Sigma-Aldrich Corporation) may be used. When the curable composition contains polyvinyl phenol, the coatability of the curable composition tends to be improved, and the dielectric constant of a cured product tends to be increased.

In the present embodiment, a curable composition satisfying the condition that the ratio of the sum of the mass of the first organic compound (a) and the second organic compound (b) to the total sum of the mass of the first organic compound (a), the second organic compound (b) and the polyvinyl phenol (d) is 50 mass % to 100 mass %, and the ratio of the mass of the second organic compound (b) to the total sum of (a), (b) and (d) is 10 mass % to 30 mass %, can be used.

The curable composition of the present embodiment may be used in combination with various fillers within the range that does not impair the advantages of the present invention. When the curable composition is used in combination with a filler, the curable composition functions as the binder of the filler, and physical properties due to the filler can be further imparted to an insulator, which will be formed.

According to the curable composition as described above, an insulator, which will be formed, has both excellent insulation properties and excellent dielectric properties.

In the above-mentioned embodiment, it has been described that the curable composition contains the polyvinyl phenol (d), but the curable composition may not contain the polyvinyl phenol (d). Alternatively, the curable composition may contain other polymers instead of the polyvinyl phenol (d).

Modified Embodiment

The curable composition of the present embodiment may further include the following (e): (e) a third organic compound represented by Formula (3) below.

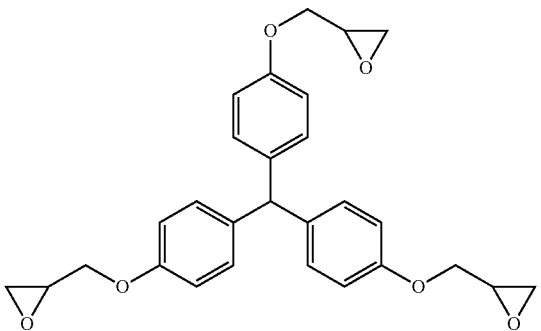

(3)

A specific example of the third organic compound (e) may include tris(4-hydroxyphenyl)methane triglycidyl ether (413305, manufactured by Sigma-Aldrich Corporation).

When the curable composition contains the third organic compound (e), the hardness of a cured product, which will be obtained, decreases. As a result, for example, if a film-like cured product is formed using the curable composition, flexibility can be imparted to the cured product, and the cured product cannot be easily damaged.

In the present embodiment, a curable composition satisfying the condition that the ratio of the sum of the mass of the first organic compound (a), the second organic compound (b), and the third organic compound (e) to the total sum of the mass of the first organic compound (a), the second organic compound (b), the polyvinyl phenol (d), and the third organic compound (e) is 50 mass % to 100 mass %, and the ratio of the mass of (b) to the total sum of (a), (b), (d), and (e) is 10 mass % to 30 mass %, can be used.

Even when the curable composition according to the modified embodiment is used, an insulator, which will be formed, has both excellent insulation properties and excellent dielectric properties.

Even in the above-mentioned modified embodiment, the curable composition may not contain the polyvinyl phenol (d). Alternatively, the curable composition may contain other polymers instead of the polyvinyl phenol (d).

(Manufacturing Method of Laminate, Laminate)

Hereinafter, a method of manufacturing a laminate according to the present embodiment and a laminate will be described with reference to FIGS. 1A to 1C. In all the following drawings, for ease of understanding the drawings, dimensions, proportions, and the like of each component are appropriately varied.

Figure 1B:
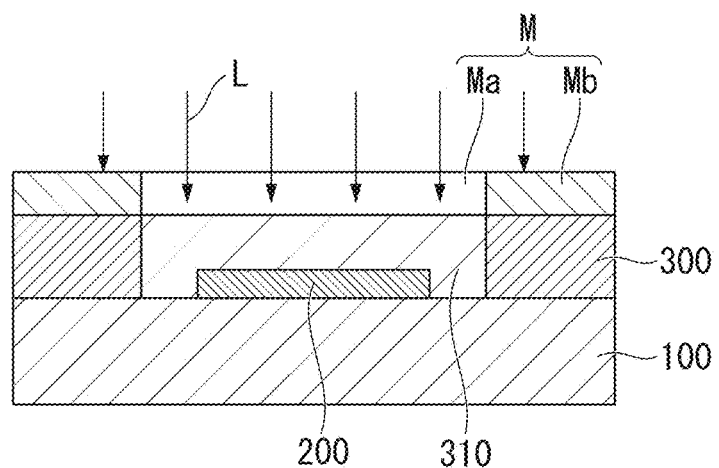
FIG. 1B is a process view showing the method of manufacturing the laminate according to the first embodiment.
Figure 1C:
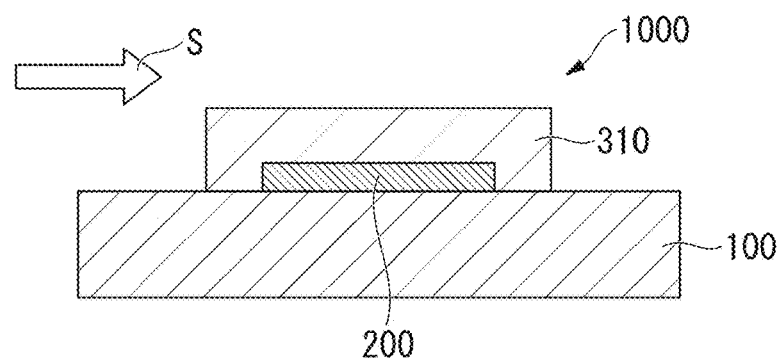
FIG. 1C is a process view showing the method of manufacturing the laminate according to the first embodiment.

FIGS. 1A to 1C are process views showing a method of manufacturing a laminate according to the present embodiment.

First, as shown in FIG. 1A, a solution in which the aforementioned curable composition is dissolved in an organic solvent (hereinafter, referred to as "a raw material solution") is applied over a conductive layer 200 formed on a substrate 100, and the solvent is removed, thereby forming a coating film 300.

Examples of the formation material of the substrate 100 may include: inorganic materials, such as glass, quartz glass, and silicon nitride; and organic materials (resin materials), such as acrylic resins, polycarbonate resins, polyester resins such as polyethylene terephthalate (PET) and polybutylene terephthalate (PBT).

As the conductive layer 200, wirings and electrodes can be exemplified. Examples of the formation material of the conductive layer 200 may include conductive polymers, metals such as Al, Ag and Au, and alloys. Generally known formation materials can be used in addition to these formation materials.

The coating film 300 is formed by applying the raw material solution and then removing the solvent. As the method of applying the raw material solution, generally known methods, such as spin coating, dip coating, spray coating, roll coating, brushing, flexographic printing, inkjet printing, and screen printing, may be exemplified.

In addition, as the solvent dissolving the curable composition, various organic solvents can be used. Examples of the organic solvent may include: alcohols, such as methanol, ethanol, 1-propanol, and 2-propanol (isopropyl alcohol (IPA)); ethers, such as propylene glycol monomethyl ether acetate (PGMEA); aromatic hydrocarbons, such as toluene and xylene; nitriles such as acetonitrile; esters such as acetic acid ester; ketones, such as acetone, methyl ethyl ketone, methyl isobutyl ketone, and cyclohexanone. These organic solvents may be used alone or in a mixture of two or more.

In order to remove a solvent from the applied raw material solution, a method of volatilizing the solvent using generally known operations such as heating, air blow and depressurization can be used. These operations may be used in a combination of two or more. In addition, the film obtained by removing a solvent from the raw material solution is prebaked, thereby forming the non-patterned coating film 300. The prebaking is performed, for example, by heating the film obtained by removing a solvent from the raw material solution at 105° C. for 5 minutes.

Next, as shown in FIG. 1B, the coating film 300 is irradiated with ultraviolet L (light) through a mask M provided with an opening Ma in a region overlapping the conductive layer 200 in a plan view and having a light shielding portion Mb around the opening Ma, so as to allow the coating film 300 to be exposed to light. The ultraviolet L is light having an absorption wavelength of the photocationic polymerization initiator included in the curable composition. For example, in the mask exposure of the present embodiment, ultraviolet of i-line ray (365 nm) is irradiated at an irradiation intensity of 500 mJ/cm$^2$. Accordingly, a photocationic polymerization reaction proceeds in the coating film 300, and the latent image of an insulator layer 310 is formed on the coating film 300.

Here, in order to accelerate a curing reaction by photocationic polymerization, a heat treatment may be performed in a temperature range of 100° C. to 120° C. for 10 minutes. This heat treatment may be performed simultaneously with the irradiation of ultraviolet L, and may also be performed after the irradiation of ultraviolet L.

Next, as shown in FIG. 1C, the coating film 300 subjected to mask exposure as shown in FIG. 1B is developed using an organic solvent as a developer S. The developing time, for example, may be set to 10 seconds.

The solubility of the exposed region (insulator layer 310) of the coating film 300 in the developer S relatively decreases compared to that of the non-exposed region in the coating film 300, because photocationic polymerization proceeds and the molecular weight increases. Therefore, the non-exposed region of the coating film 300 is dissolved and developed by the developer S.

After the development, the substrate is washed with water, and heat treatment is performed in a temperature range of 100° C. to 120° C. for 30 to 60 minutes, to thereby form the insulator layer 310. When the heat treatment temperature is low, the heat treatment time may be longer. For example, when a heat treatment is performed at 105° C. or lower, the heat treatment may be performed for 60 minutes. In this way, it is possible to form a laminate 1000 having the insulator layer 310 covering the conductive layer 200.

According to the method of manufacturing a laminate, as described above, a curable composition capable of forming an insulator having both excellent insulation properties and excellent dielectric properties is used, and therefore it is possible to easily manufacture a high-performance laminate.

The above-described laminate can be a high-performance laminate because a curable composition capable of forming an insulator having both excellent insulation properties and excellent dielectric properties is used.

As the laminate 1000 having a laminated structure manufactured in this way, a wiring board, a condenser, and the like, each having a multi-layer interconnect structure, are exemplified.

Second Embodiment (Manufacturing Method of Transistor, Transistor)

Next, a method of manufacturing a transistor according to a second embodiment of the present invention and a transistor will be described with reference to FIGS. 2 to 8B.

Figure 2:
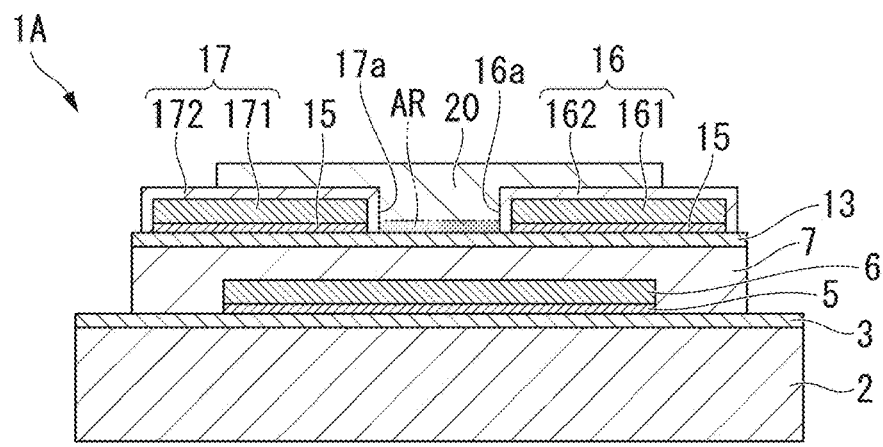
FIG. 2 is a schematic cross-sectional view showing a transistor of a second embodiment.

FIG. 2 is a schematic cross-sectional view showing a transistor manufactured by the method of manufacturing a transistor according to the present embodiment, and a transistor according to the present embodiment. A transistor 1A is a so-called bottom-contact type transistor. In the following description, there will be described an organic transistor using an organic semiconductor as the formation material of a semiconductor layer, but the present invention is also applicable to an inorganic transistor using an inorganic semiconductor as the formation material of a semiconductor layer.

The transistor 1A includes a substrate 2, base films 3 and 13, electroless plating catalysts 5 and 15, a gate electrode 6, an insulator layer 7, a source electrode 16, a drain electrode 17, and an organic semiconductor layer (semiconductor layer) 20. In the transistor 1A, the layer of a combination of the insulator layer 7 and the base film 13 refers to "a layer containing an insulator layer".

As the substrate 2, any of a substrate having optical transparency and a substrate not having optical transparency can be used. For example, the substrate 2 can be made of any one of: inorganic materials such as glass, quartz glass, and silicon nitride; and organic polymers (resins), such as acrylic resins, polycarbonate resins, and polyester resins (for example, polyethylene terephthalate (PET), polybutylene terephthalate (PBT), and the like).

The formation material of these substrates 2 does not form a metallic bond together with a metal-made plating film formed as a result of electroless plating. For this reason, in the present embodiment, the formation material of these substrates 2 is treated as a poor plating material on which a plating film is not easily formed directly, and the formed plating film is easily stripped. Due to the similar reason, if the plating film is made of an easily-strippable material, for example, a composite material of the above-mentioned material and the like can also be similarly used as the formation material of the substrate 2.

The base film 3 is a gate base film in the present invention. The base film 3 is formed over the entire surface of the main side of the substrate 2, and part of the surface of the base film 3 is selectively provided with a catalyst (electroless plating catalyst) 5. The catalyst 5 is a catalyst for reducing metal ions contained in a plating solution for electroless plating. As the catalyst, silver, metal palladium, and the like are exemplified. In the present embodiment, metal palladium is used.

The base film 3 is a film capable of capturing a metal that is the above-mentioned catalyst 5, and a silane coupling agent having a group capable of capturing the metal is used as the formation material of the base film 3. The base film 3 is formed by applying a liquid product containing such a silane coupling agent onto the main side of the substrate 2.

The "silane coupling agent", which is the formational material of the base film 3, is a compound in which a group capable of capturing the metal (catalyst 5) and a group capable of being bonded to the substrate 2 are bonded to a silicon atom.

Here, the "group capable of capturing the metal" refers to a group that can capture the metal (catalyst 5) or ions of this metal, for example, by an ion bond or a coordinate bond. As this group, a group having a nitrogen atom or a sulfur atom is exemplified. Examples of the group having a nitrogen atom or a sulfur atom may include an amino group, a urea group, a thiol group (or a mercapto group), a thiocarbonyl group, a thiourea group, and a group obtained by removing one or more hydrogen atoms bonded to a heterocyclic compound containing a nitrogen atom or a sulfur atom. Examples of the "heterocyclic compound containing a nitrogen atom or a sulfur atom" include: monocyclic aromatic heterocyclic compounds, such as pyrrole, imidazole, pyridine, pyrimidine, and thiophene; polycyclic aromatic heterocyclic compounds, such as indole and benzothiophene; and non-aromatic heterocyclic compounds in which two or more carbon atoms in an aromatic ring of each of these aromatic compounds are hydrogenated.

As the "group capable of being bonded to the substrate 2", a hydroxyl group and an alkoxy group of 1 to 6 carbon atoms are exemplified.

Specific examples of the compound that can be used as the formation material of the base film 3 may include N-cyclohexyl-aminopropyltrimethoxysilane, bis(3-(trimethoxysilyl)propyl)ethylenediamine, 1-(3-(trimethoxysilylpropyl))urea, bis(3-trimethoxysilylpropyl))urea, 2,2-dimethoxy-1,6-diaza-2-silacyclooctane, N-(3-(trimethoxysilyl propyl))-4,5-dihydroimidazole, bis(3-(trimethoxysilyl)propyl)thiourea, 3-trimethoxysilylpropanethiol, and polyethyleneimine modified with a trimethoxysilylpropyl group.

Among these, as the silane coupling agent, a silane coupling agent having an amino group as the "group capable of capturing metal" is preferable, and a silane coupling agent, which is a primary amine or a secondary amine ("group capable of capturing metal" is a group represented by $—NH_2$ or $—NH—$), is more preferable. In the following description, as the base film 3, a base film formed by using a silane coupling agent as a primary amine will be described.

The gate electrode 6 is a metal electrode formed on the surface of the catalyst 5, and, as described later, is formed of a metal deposited on the surface of the catalyst 5 by electroless plating. As the material of the gate electrode 6, nickel phosphorus (NiP) or copper (Cu) is exemplified.

The insulator layer 7 electrically insulates the gate electrode 6 having insulating properties from the source electrode 16 and the drain electrode 17. In the insulator layer 7 of the present embodiment, the above-mentioned curable composition in the first embodiment is used as a formation material.

The base film 13 is formed on the entire upper surface of the insulator layer 7. The base film 13 is a source base film and is a drain base film in the present invention, and the source base film and the drain base film are formed as a continuous film. The base film 13 is formed over the entire surface of the main side of the substrate 2, and part of the surface of the base film 13 is selectively provided with a catalyst (catalyst for electroless catalyst) 15. The formation material of the catalyst 15 may be the same as that of the above-mentioned catalyst 5.

The formation material of the base film 13 is the same as that of the above-mentioned base film 3, but the formation materials of the base film 3 and the base film 13 may be different from each other. In the following description, a case where the base film 13 is formed by using a silane coupling agent as a primary amine which is the same as that used for the base film 3 will be described.

In the drawing, it is shown that the base film 13 is formed on the entire upper surface of the insulator layer 7, but the base film 13 may be selectively formed on only a location where the catalyst 15 is provided. In this case, a silane coupling agent, which is a formation material of the base film 13, is selectively applied to the upper surface of the insulator layer 7 using a generally known method, and thereby it is possible to selectively form the base film 13. Further, in the upper surface of the insulator layer 7, first, the silane coupling agent may be applied to a region larger than the region forming the base film 13, and then a film formed at a portion protruding from the region forming the base film 13 may be irradiated with ultraviolet to thereby decompose and remove the silane coupling agent to selectively form the base film 13.

The source electrode 16 and the drain electrode 17 are metal electrodes formed on the surface of the catalyst 15.

The source electrode 16 has a first electrode 161 and a second electrode 162 covering the surface of the first electrode 161. Similarly, the drain electrode 17 has a third electrode 171 and a fourth electrode 172 covering the surface of the third electrode 171.

The first electrode 161 and the third electrode 171, similarly to the above-mentioned gate electrode 6, are formed by electroless plating. As the material of each of the first electrode 161 and the third electrode 171, nickel phosphorus (NiP) or copper (Cu) is exemplified. In the present embodiment, it is described that nickel phosphorus (work function: 5.5 eV) is used as the formation material of each of the first electrode 161 and the third electrode 171. Here, the first electrode 161 and the third electrode 171 may each be formed using a different material.

The second electrode 162 and the fourth electrode 172 are metal plating layers, each being formed over the entire surface of each of the first electrode 161 and the third electrode 171, the surface not being in contact with the catalyst 15. That is, the second electrode 162 and the fourth electrode 172 are provided to cover lateral sides 16a and 17a (opposing surfaces) facing each other in the source electrode 16 and the drain electrode 17.

As the formation material of each of the second electrode 162 and the fourth electrode 172, a metal material having a work function in which electron transfer (or hole transfer) is easy in relation to the HOMO/LUMO level of the formation material of a semiconductor layer 20 to be described later is used. In the present embodiment, it is described that gold (work function: 5.4 eV) is used as the formation material of each of the second electrode 162 and the fourth electrode 172. Here, the second electrode 162 and the fourth electrode 172 may each be formed using a different material.

The semiconductor layer 20 is provided on the surface of the base film 13 between the source electrode 16 and the drain electrode 17, and is formed in contact with the source electrode 16 and the drain electrode 17. Specifically, the semiconductor layer 20 is provided in contact with the lateral side 16a of the source electrode 16 and the lateral side 17a of the drain electrode 17, and is in contact with the second electrode 162 and the fourth electrode 172.

As the formation material of the semiconductor layer 20, generally known organic semiconductor materials can be used. Examples of the semiconductor materials may include: p-type semiconductors, such as copper phthalocyanine (CuPc), pentacene, rubrene, tetracene, and P3HT (poly(3-hexylthiophene-2,5-diyl)); and n-type semiconductors, such as fullerenes such as $C_{60}$ and perylene derivatives such as PTCDI-C8H (N,N'-dioctyl-3,4,9,10-perylene tetracarboxylic diimide). Among these, soluble pentacene such as TIPS pentacene (6,13-bis(triisopropylsilylethynyl) pentacene) or an organic semiconductor polymer such as P3HT is soluble in an organic solvent such as toluene and can be used in forming the semiconductor layer 20 by a wet process, which is preferable. In the present embodiment, it will be described that TIPS pentacene (HOMO level: 5.2 eV), which is a p-type semiconductor, is used as the formation material of the semiconductor layer 20.

Further, the formation material of the semiconductor layer 20 is not limited to organic semiconductor materials, and generally known inorganic semiconductor materials can also be used as the formation material of the semiconductor layer 20.

In this transistor 1A, the gate electrode 6, the source electrode 16, and the drain electrode 17, which are formed by electroless plating, are formed on the base films 3 and 13 (gate base film, source base film, and drain base film), which are formed by using a silane coupling agent as a formation material. For example, when these electrodes are formed in the region having an uneven shape, an uneven shape is imparted to each of these electrodes in response to unevenness of a base. In this regard, if the distance between the electrodes laminated through an insulator layer is not constant, there is a possibility that the insulation is damaged and leak current is generated at the position where the distance between the gate electrode and the source electrode or the distance between the gate electrode and the drain electrode becomes closer to each other. Further, if the base has an uneven shape, there is a possibility that an uneven shape is imparted even to the channel region (represented by AR in FIG. 2) of the semiconductor layer overlapping the gate electrode in a plan view, and the migration distance of a carrier in the channel region becomes longer, thereby deteriorating the performance of the transistor 1A.

However, in the transistor 1A of the present embodiment, since the base films 3 and 13 are formed by using a silane coupling agent as a formation material and a base film containing a filler component capable of roughening the surface of the substrate is not used, these base films become smooth films. Therefore, uneven shapes are not formed by forming the base films 3 and 13, and the problems caused by the uneven shapes do not occur, and therefore the transistor 1A becomes a high-performance transistor.

Hereinafter, the method of manufacturing the above-mentioned transistor 1A will be described with reference to FIGS. 3A to 7D.

Figure 3A:
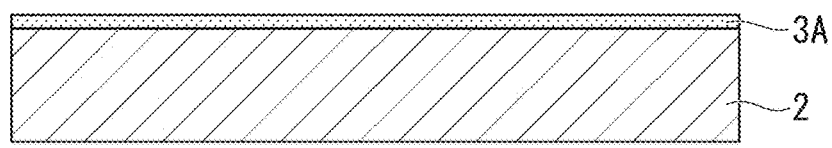
FIG. 3A is a process view showing a manufacturing method of the second embodiment.

First, as shown in FIG. 3A, a liquid product, which is obtained, if necessary, by diluting the above-mentioned silane coupling agent with an organic solvent, is applied onto the surface of a substrate 2 to form a coating film 3A. As the method of applying the liquid product, generally known methods, such as spin coating, dip coating, spray coating, roll coating, brushing, flexographic printing, and screen printing, may be exemplified.

Here, it will be described that 3-aminopropyltriethoxysilane, which is a primary amine, is used as the silane coupling agent.

As the organic solvent, various organic solvents can be used as long as they can dissolve the silane coupling agent. Among these organic solvents, a polar solvent can be preferably used. Examples of the solvent that can be used may include: alcohols, such as methanol, ethanol, 1-propanol, and 2-propanol (isopropyl alcohol (IPA)); ethers, such as propylene glycol monomethyl ether acetate (PGMEA); aromatic hydrocarbons, such as toluene; nitriles such as acetonitrile; esters such as acetic acid ester; ketones, such as acetone, methyl ethyl ketone, and methyl isobutyl ketone.

Figure 3B:
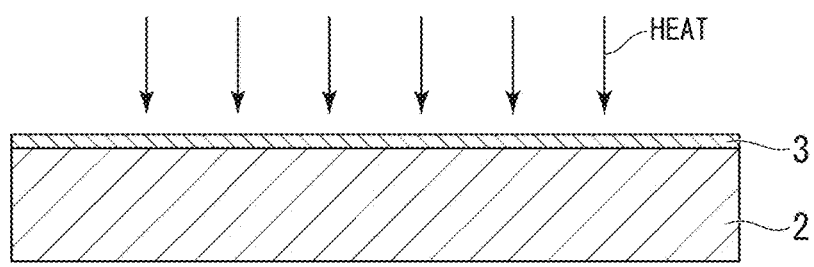
FIG. 3B is a process view showing the manufacturing method of the second embodiment.

Next, as shown in FIG. 3B, the organic solvent is volatilized and removed by a heat treatment to form a base film 3. The base film 3 formed in this manner is a silane coupling agent layer having extremely thin film thickness, and therefore becomes a transparent film in which light scattering does not easily occur. Therefore, for example, if the transistor manufactured by the method of the present embodiment is provided on a substrate having optical transparency, it is possible to maintain the optical transparency as a combination of the substrate 2 and the base film 3 even when the base film 3 is formed on the entire surface of the substrate 2, and it is possible to easily form the film.

Figure 4A:
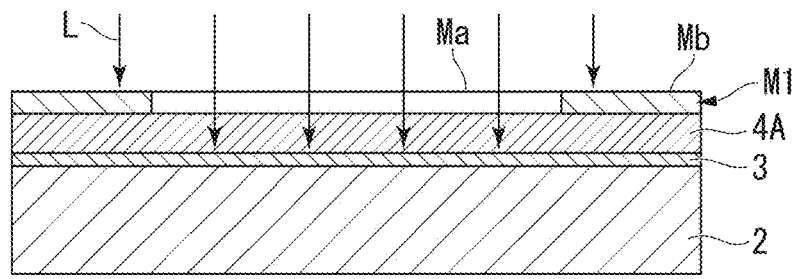
FIG. 4A is a process view showing the manufacturing method of the second embodiment.

Next, as shown in FIG. 4A, a resist material is applied onto the base film 3, and is then prebaked to thereby form a resist layer 4A that is not patterned. Here, as the resist material, a positive photoresist is used.

Thereafter, the resist layer 4A is irradiated with ultraviolet L through a mask M1 including an opening Ma provided at the position corresponding to the region forming a metal electrode and including a light shielding portion Mb provided in the region not forming the metal electrode, so as to expose the resist layer 4A to light.

Figure 4B:
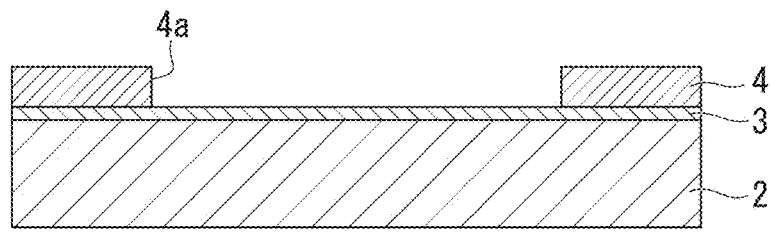
FIG. 4B is a process view showing the manufacturing method of the second embodiment.

Next, as shown in FIG. 4B, the resist layer irradiated with ultraviolet is developed by a developer that dissolves the resist layer to thereby form a resist layer 4 provided with an opening 4a.

Figure 4C:
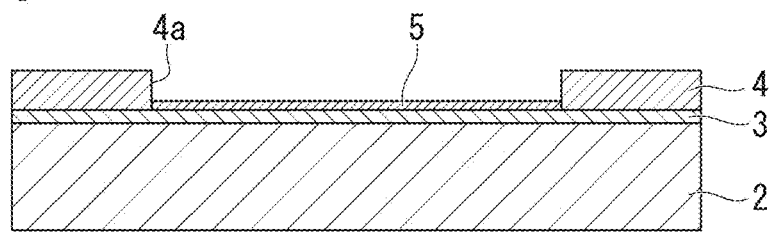
FIG. 4C is a process view showing the manufacturing method of the second embodiment.

Next, as shown in FIG. 4C, a catalyst 5 used in electroless plating is captured on the surface of the base film 3 exposed through the opening 4a formed in the resist layer 4. Specifically, a metal, which is the catalyst 5, is captured on the base film 3 by contacting a colloidal solution of a divalent palladium salt.

A general electroless plating process of a resin proceeds in the order of washing, etching, catalyst imparting, and then electroless plating. Here, the "catalyst imparting" is a process of attaching a metal such as palladium (Pd), serving as an electroless plating reaction initiator (catalyst), to the surface of the region for carrying out plating. Generally, the "catalyst imparting" includes a process of bringing a colloidal solution of a divalent palladium salt and a divalent tin (Sn) salt into contact with a substrate to be attached by palladium and then immersing the substrate coated with the colloidal solution into an acid or alkali solution, called an accelerator, to thereby reduce the divalent palladium to zero-valent palladium, thereby activating the catalyst.

In contrast, as described in the present embodiment, it was confirmed by the inventors that, if the silane coupling agent, which is a formation material of a base film, is a primary amine or a secondary amine, the reduction treatment using the above-mentioned accelerator is not required (which will be described later). Therefore, when a primary amine or a secondary amine is used as the silane coupling agent, the operation of electroless plating is simplified.

In the present embodiment, since 3-aminopropyltriethoxysilane, which is a primary amine, is used as the formation material of the base film 3, a reduction treatment is not required, and the operation is simplified.

On the other hand, when the silane coupling agent is a tertiary amine or a silicon compound having another "group capable of capturing a metal", a colloidal solution of a divalent palladium salt is applied, and then a normal treatment (activating process) using the above-mentioned accelerator is performed. Thereby, it is possible to capture a catalyst 5 for electroless plating on the base film 3.

Figure 4D:
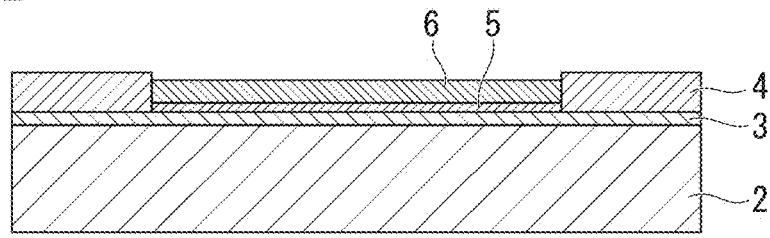
FIG. 4D is a process view showing the manufacturing method of the second embodiment.

Next, as shown in FIG. 4D, an electroless plating solution is brought into contact with the catalyst 5, and thereby metal ions dissolved in the electroless plating solution is reduced and deposited on the surface of the catalyst 5, so as to selectively form a gate electrode 6 containing nickel phosphorus as a formation material in the opening 4a. When the silane coupling agent is a primary amine or a secondary amine, the catalyst 5 is immersed in the electroless plating solution without performing the activation using the accelerator, and thereby the surface of the catalyst 5 is plated. Therefore, it can be indirectly confirmed that metal palladium is captured on the surface of the base film 3.

Figure 4E:
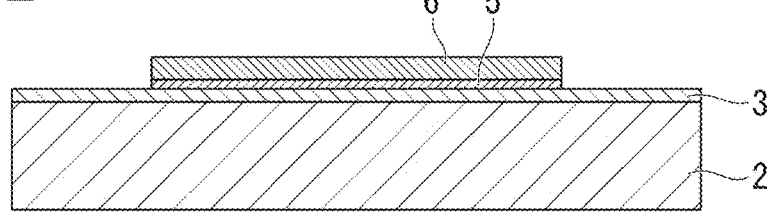
FIG. 4E is a process view showing the manufacturing method of the second embodiment.

Next, as shown in FIG. 4E, the entire surface of the remaining resist layer is exposed to ultraviolet, and then the resist layer is removed by a generally known developer, so as to form the gate electrode 6.

Figure 5A:
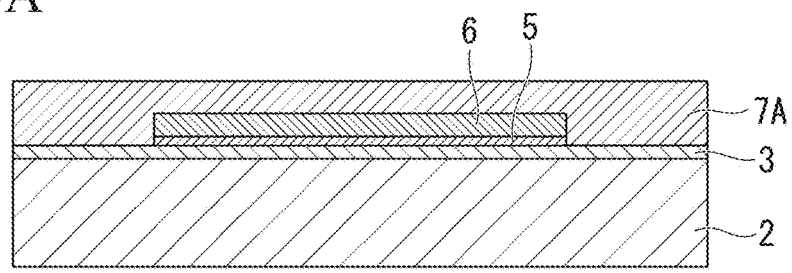
FIG. 5A is a process view showing the manufacturing method of the second embodiment.

Next, as shown in FIG. 5A, a solution (raw material solution), in which the curable composition of the first embodiment is dissolved in an organic solvent, is applied to the surface of the base film 3 to cover the gate electrode 6. As the application method, the above-mentioned method can be used.

As the organic solvent, a material which is the same as that described in the first embodiment can be used.

Further, in the raw material solution, when concentration and the kind of an organic solvent are changed, the viscosity of the entire raw material solution can be adjusted, and the thickness of the coating film 7A of the raw material solution can be controlled.

In the process shown in FIG. 5A, in order to control the leak between the gate electrode 6 and the source electrode to be formed above and the leak between the gate electrode 6 and the drain electrode to be formed above, the photoresist is thickly applied such that the thickness of the coating film 7A is about several hundreds of nanometers. Here, the thickness of the coating film 7A is not limited thereto.

Figure 5B:
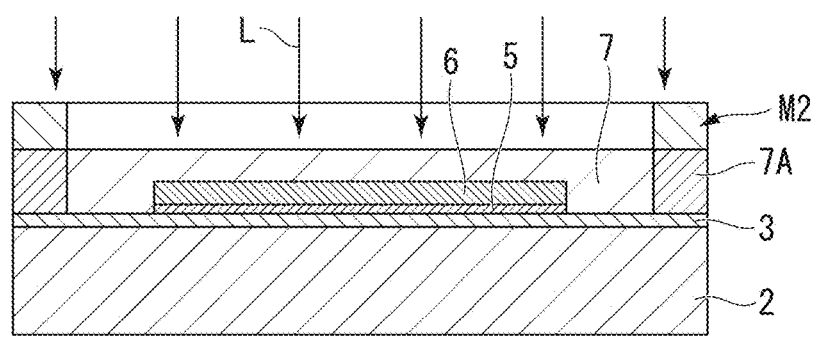
FIG. 5B is a process view showing the manufacturing method of the second embodiment.

Next, as shown in FIG. 5B, the coating film 7A is irradiated with ultraviolet L through a mask M2 provided with an opening corresponding to the region forming an insulator layer 7 to cure the curable composition, thereby forming the insulator layer 7. In this case, in order to accelerate the curing reaction of the curable composition, a heat treatment can be performed simultaneously with the ultraviolet irradiation or after the ultraviolet irradiation.

Figure 5C:
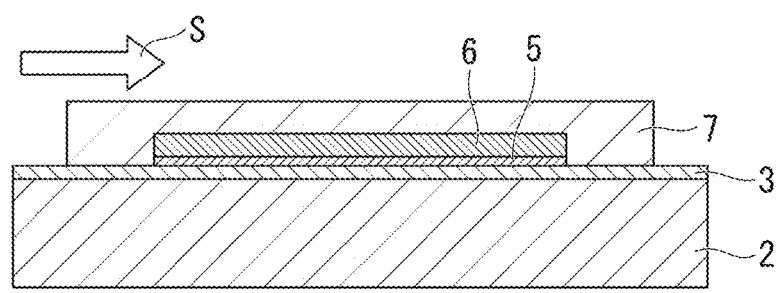
FIG. 5C is a process view showing the manufacturing method of the second embodiment.

Next, as shown in FIG. 5C, the coating film 7A is developed by an organic solvent (developer S) that dissolves the coating film 7A to thereby remove the uncured coating film and form an insulator layer 7 that is patterned.

Here, in order to improve the adhesiveness between the insulator layer 7 and the gate electrode 6, the silane coupling agent may be applied to cover the surface including the gate electrode 6 before the application of the raw material solution.

Figure 6A:
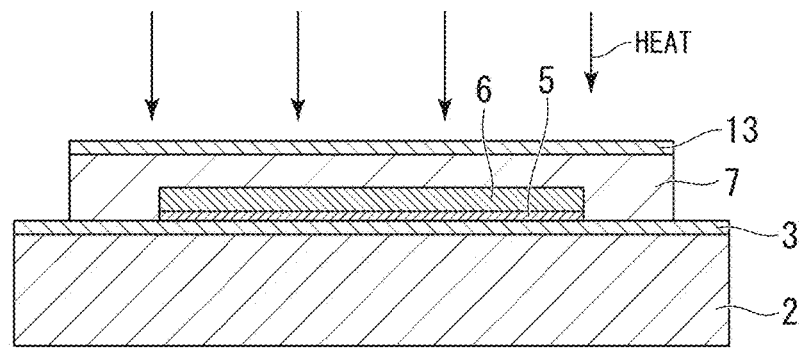
FIG. 6A is a process view showing the manufacturing method of the second embodiment.

Next, as shown in FIG. 6A, a liquid product, which is obtained, if necessary, by diluting the above-mentioned silane coupling agent with an organic solvent, is applied onto the entire upper surface of the insulator layer 7, and then a heat treatment is performed to volatilize and remove the organic solvent, so as to form a base film 13. The silane coupling agent and the organic solvent may be the same as those used in the formation of the base film 3 described above.

Figure 6B:
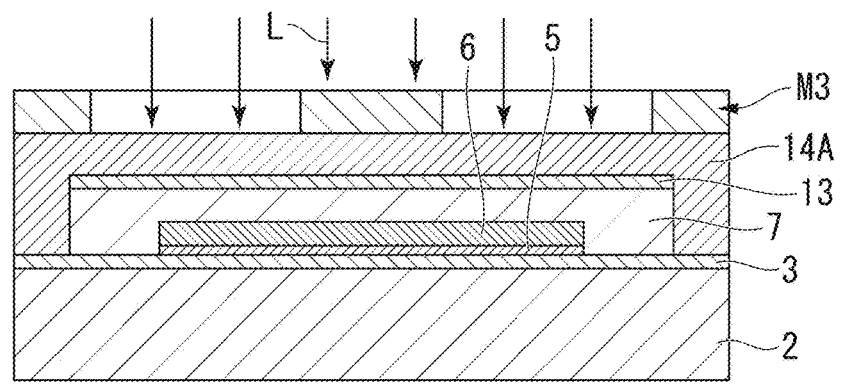
FIG. 6B is a process view showing the manufacturing method of the second embodiment.

Next, as shown in FIG. 6B, a resist material is applied over the insulator layer 7 and the base film 13, and is then prebaked to thereby form a resist layer 14A that is not patterned. Here, as the resist material, a positive photoresist is used.

Thereafter, the resist layer 14A is irradiated with ultraviolet L through a mask M3 provided with an opening corresponding to the region forming a source electrode and a drain electrode, so as to expose the resist layer 14A to light.

Figure 6C:
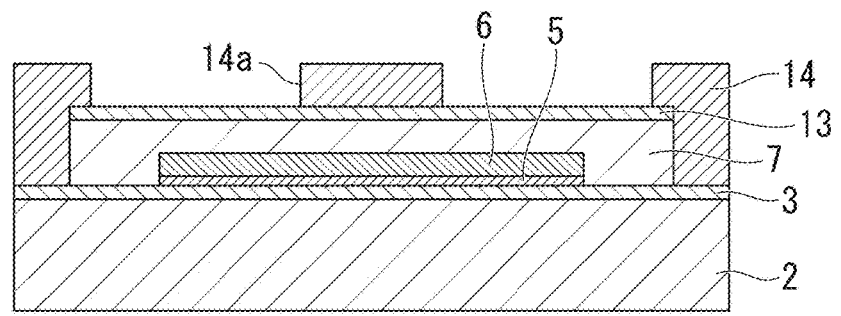
FIG. 6C is a process view showing the manufacturing method of the second embodiment.

Next, as shown in FIG. 6C, the resist layer irradiated with ultraviolet is developed by a developer that dissolves the resist layer to thereby form a resist layer 14 provided with an opening 14a.

Figure 7A:
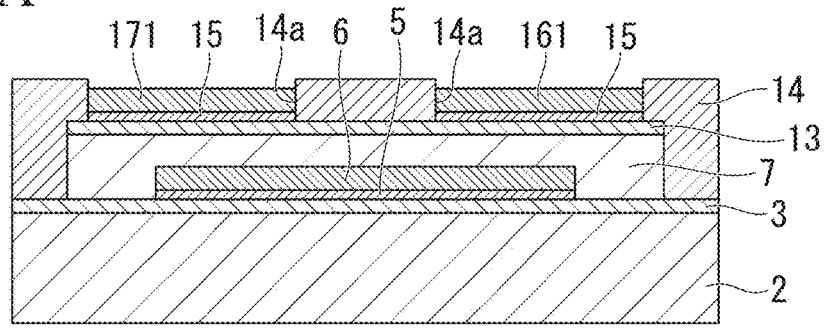
FIG. 7A is a process view showing the manufacturing method of the second embodiment.

Next, as shown in FIG. 7A, a colloidal solution of a divalent palladium salt is made to come into contact with the base film 13 exposed through the opening 14a, thereby capturing the catalyst 15 used in electroless plating to the surface of the base film 13. Thereafter, an electroless plating solution is made to come into contact with the catalyst 15, and thereby metal ions dissolved in the electroless plating solution are reduced and deposited on the surface of the catalyst 15, so as to selectively form a first electrode 161 and a third electrode 171 made of nickel phosphorus in the opening 14a.

Figure 7B:
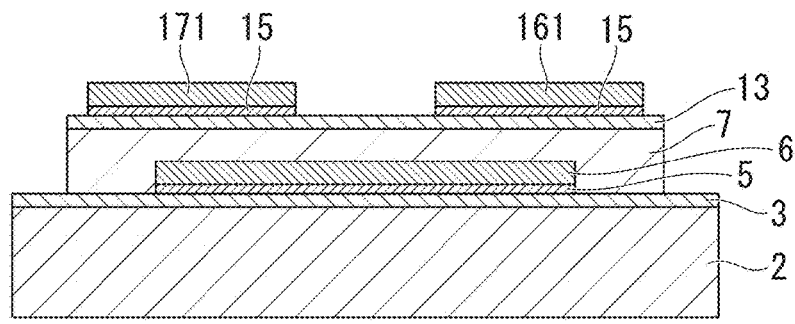
FIG. 7B is a process view showing the manufacturing method of the second embodiment.

Next, as shown in FIG. 7B, the entire surface of the remaining resist layer is exposed to ultraviolet, and then the resist layer is removed by a generally known developer, thereby forming the first electrode 161 and the third electrode 171.

Figure 7C:
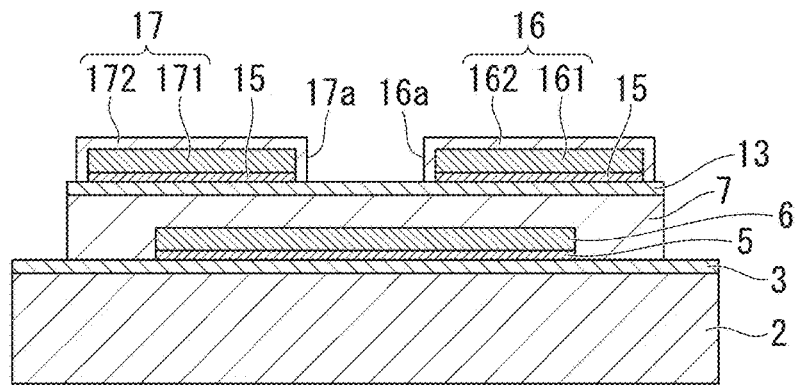
FIG. 7C is a process view showing the manufacturing method of the second embodiment.

Next, as shown in FIG. 7C, the entire body is immersed into a gold plating bath for substitution to allow the surface of the first electrode 161 and the third electrode 171 to be substituted and deposited with gold, and is further immersed into a gold plating bath for reduction to thereby form a second electrode 162 and a fourth electrode 172, which are plated with gold, on the surface of the first electrode 161 and the third electrode 171. In this way, a source electrode 16 and a drain electrode 17 are formed.

Figure 7D:
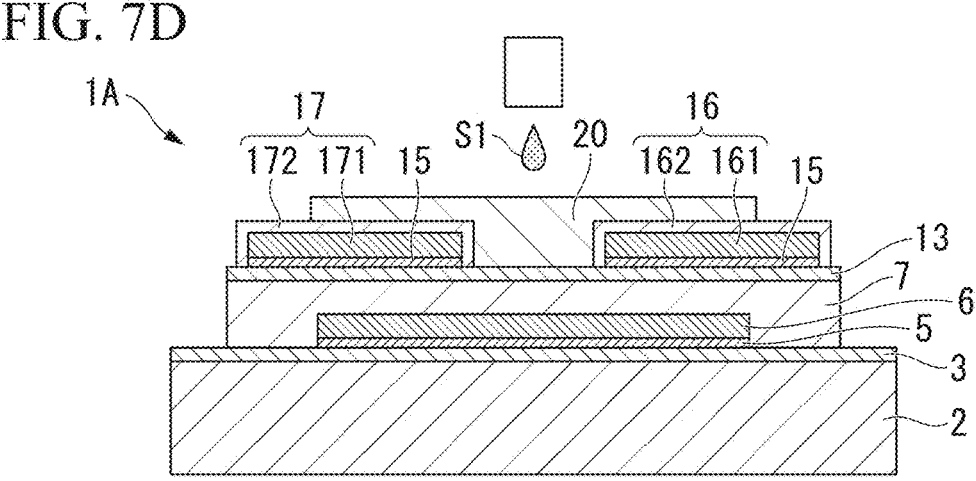
FIG. 7D is a process view showing the manufacturing method of the second embodiment.

Next, as shown in FIG. 7D, a solution S1, in which an organic semiconductor material soluble in an organic solvent, such as TIPS pentacene, is dissolved in the organic solvent, is applied between the source electrode 16 and the drain electrode 17, and is dried to thereby form a semiconductor layer 20. Here, the semiconductor layer 20 is formed by a wet method, but can also be formed by a sublimation method, a transfer method, or the like.

In this way, it is possible to manufacture the transistor 1A.

According to the above-mentioned method of manufacturing a transistor, since a curable composition capable of forming an insulator layer having both excellent insulation properties and excellent dielectric properties is used, it is possible to easily manufacture a high-performance transistor.

Since the above-mentioned transistor is manufactured using a curable composition capable of forming an insulator layer having both excellent insulation properties and excellent dielectric properties, the transistor can be a high-performance transistor.

Further, since the base films 3 and 13 are formed by using a silane coupling agent as a formation material and are smooth films, problems caused by the uneven shapes of the base films do not occur, and a high-performance transistor can be obtained.

Further, since the resist layer 14 is previously removed before the formation of the second electrode 162 and the fourth electrode 172, the second electrode 162 and the fourth electrode 172 can be surely formed even on the lateral side 16a of the source electrode 16 and the lateral side 17a of the drain electrode 17. Therefore, in the manufactured transistor 1A, electric current easily flows between the semiconductor layer 20 and the source electrode 16 or between the semiconductor layer 20 and the drain electrode 17 at the time of driving, and the transistor 1A can be well driven.

Further, since the first electrode 161 and the third electrode 171 are covered with the second electrode 162 and the fourth electrode 172, the temporal corrosion of the first electrode 161 and the third electrode 171 is suppressed, and there is also an advantage in that the performance of the transistor can be stably maintained.

Further, when a curable composition containing the above-mentioned third organic compound (e) is used as the curable composition, which is a formation material of an insulator layer, it is possible to impart flexibility to the insulator layer to be formed.

Therefore, the insulator layer is hardly damaged even when stress is applied, and it is possible to make a highly reliable transistor. For example, when a flexible transistor is formed by employing a material having flexibility in a substrate, a wiring structure, or the like, damage to the insulator layer is suppressed even though the transistor is bended or flexed, and reliability is improved.

Figure 8A:
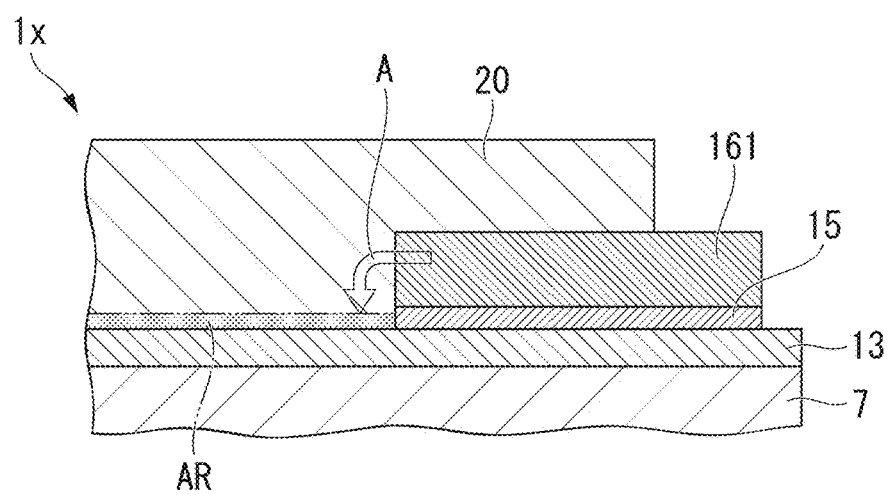
FIG. 8A is a view showing the drive status of the transistor of the second embodiment.
Figure 8B:
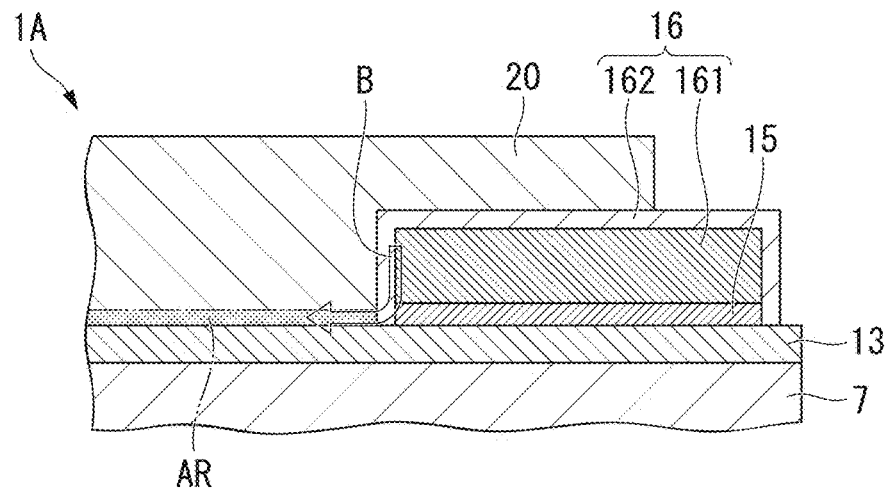
FIG. 8B is a view showing the drive status of the transistor of the second embodiment.

FIG. 8A, 8B is a schematic view showing the drive status of a transistor. FIG. 8A is a view showing a transistor 1x which has the same configuration as the transistor 1A except that it does not have the second electrode, and FIG. 8B is a view showing the transistor 1A manufactured by the method of the present embodiment.

Here, in the present embodiment, the phrase "energy level of molecular orbital used in electron transfer in the formation material of an organic semiconductor layer" refers to the energy level of HOMO in the case where the organic semiconductor layer is made of a p-type semiconductor, and refers to the energy level of LUMO in the case where the organic semiconductor layer is made of an n-type semiconductor.

First, as in the transistor 1x shown in FIG. 8A, when the transistor 1x is configured not to have the second electrode, since the gap (energy level difference) between the energy level of HOMO of the semiconductor layer 20 and the work function of the first electrode 161 becomes large, Schottky barrier occurs, and electric current hardly flows. Therefore, for example, as shown by an arrow A in FIG. 8A, it is easy to form the flow of electric current through the highly-resistant semiconductor layer 20, and it is difficult to secure a good conduction.

In contrast, as shown in FIG. 8B, in the transistor 1A, when a voltage is applied to the gate electrode (not shown), a channel region AR having a thickness of several nanometers (nm) is formed around the interface between the semiconductor layer 20 and the base film 13, enabling the conduction between the source electrode 16 and the drain electrode (not shown). In this case, the surface of the source electrode 16 is provided with the second electrode 162, which is formed using a metal material having a work function (energy level difference with HOMO of the semiconductor layer 20 is small) at which electron transfer is easier between the second electrode 162 and the formation material of the semiconductor layer 20 compared to between the second electrode 162 and the first electrode 161, and the Shottky barrier is reduced, so that electric current easily flows into the channel region AR through the first electrode 161 and the second electrode 162. FIG. 8B shows the flow of electric current using an arrow B. Therefore, it is possible to realize a high-performance transistor 1A.

Third Embodiment

Figure 9:
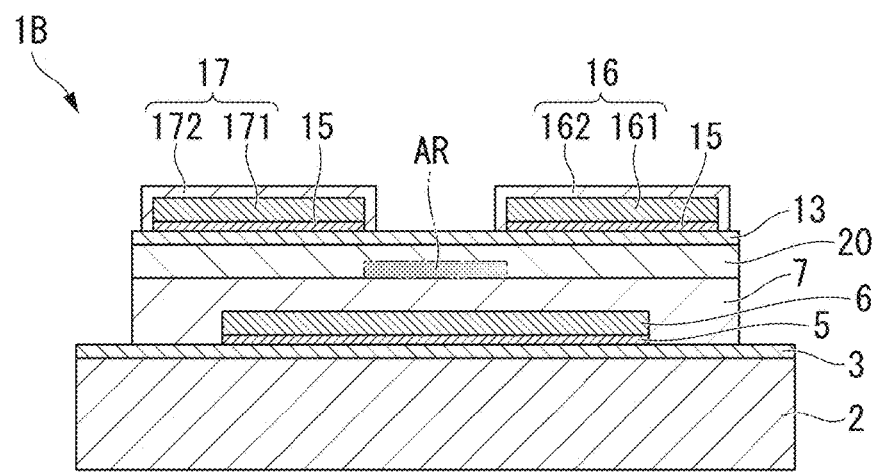
FIG. 9 is a schematic cross-sectional view showing a transistor of the second embodiment.

FIG. 9 is a schematic cross-sectional view of a transistor 1B, which is manufactured by the manufacturing method of the transistor according to a third embodiment of the present invention.

The transistor 1B of the present embodiment is partially in common with the transistor 1A of the second embodiment. The difference between the transistor 1A and the transistor 1B is that the transistor of the second embodiment is a bottom contact transistor, and the transistor 1B of the present embodiment is a top contact transistor. Accordingly, in the present embodiment, the same reference numerals for the components in common with the second embodiment are used, and detailed description of the components will be omitted.

The transistor 1B includes a semiconductor layer 20 disposed on an insulator layer 7 and having a surface on which a source electrode 16 and a drain electrode 17 are formed.

That is, a semiconductor layer 20 is formed on the entire upper surface of an insulator layer 7, and a base film 13 is formed on the entire upper surface of the semiconductor layer 20. In the transistor 1B, the layer of a combination of the insulator layer 7, the semiconductor layer 20, and the base film 13 refers to a "layer containing an insulator layer".

A catalyst 15 is selectively provided on the upper surface of the base film 13, and a source electrode 16 including a first electrode 161 and a second electrode 162 and a drain electrode 17 including a third electrode 171 and a fourth electrode 172 are formed on the upper surface. In the semiconductor layer 20, the region located in the vicinity of the upper surface of the semiconductor layer and sandwiched between the source electrode 16 and the drain electrode 17 becomes a channel region AR.

Hereinafter, the method of manufacturing the above-mentioned transistor 1B will be described with reference to FIGS. 10A to 11C.

Figure 10A:
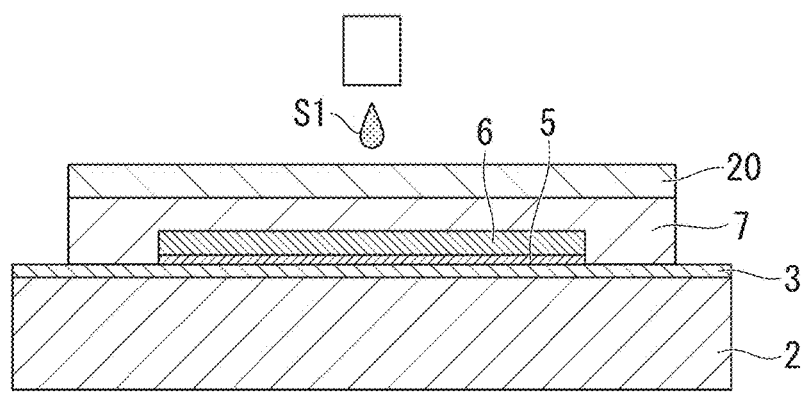
FIG. 10A is a process view showing a manufacturing method of the second embodiment.

In the manufacture of the transistor 1B, first, similarly to the second embodiment, a base film 3, a catalyst 5, a gate electrode 6, and an insulator layer 7 are laminated on the upper surface of a substrate 2. Next, as shown in FIG. 10A, a solution S1 in which an organic semiconductor soluble in an organic solvent is dissolved in the organic solvent is applied onto the insulator layer 7, and then dried to thereby form the semiconductor layer 20.

Figure 10B:
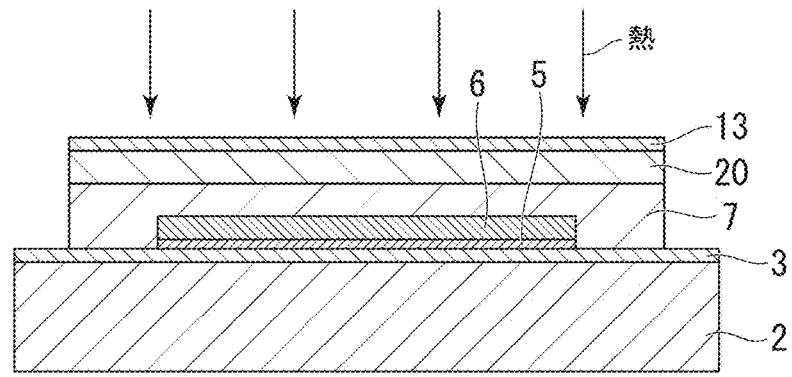
FIG. 10B is a process view showing the manufacturing method of the second embodiment.

Next, as shown in FIG. 10B, a liquid product, which is obtained, if necessary, by diluting the above-mentioned silane coupling agent with an organic solvent, is applied onto the entire upper surface of the semiconductor layer 20, and then is heat-treated to volatilize and remove the organic solvent, thereby forming a base film 13.

Figure 10C:
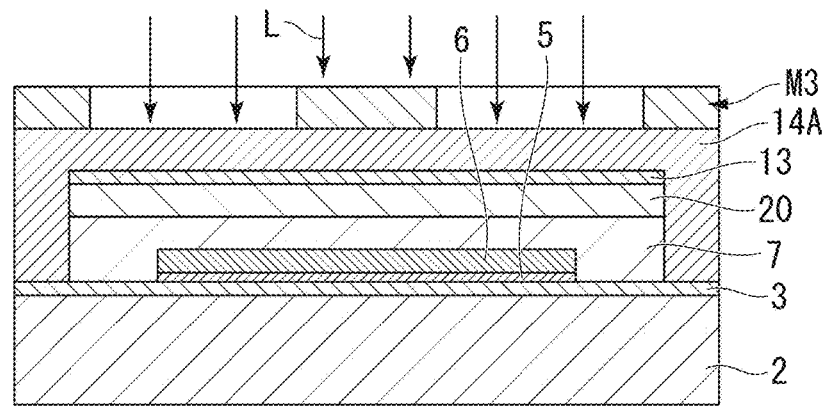
FIG. 10C is a process view showing the manufacturing method of the second embodiment.

Next, as shown in FIG. 10C, a resist material is applied over the insulator layer 7, the semiconductor layer 20, and the base film 13, and is then prebaked to thereby form a resist layer 14A that is not patterned. Thereafter, the resist layer 14A is irradiated with ultraviolet L through a mask M3 provided with an opening corresponding to the region forming a source electrode and a drain electrode, so as to expose the resist layer 14A to light.

Figure 10D:
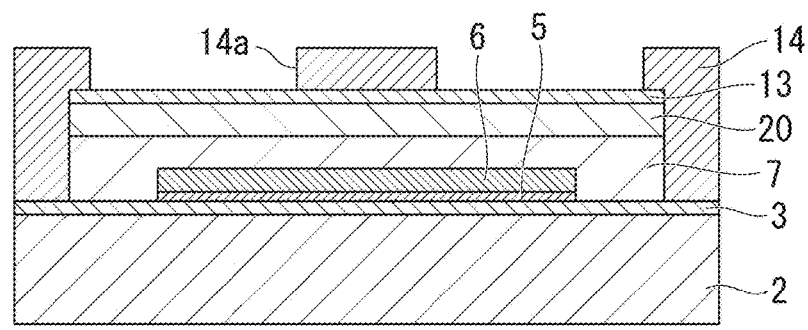
FIG. 10D is a process view showing the manufacturing method of the second embodiment.

Next, as shown in FIG. 10D, the resist layer irradiated with ultraviolet is developed by a developer dissolving the resist layer to thereby form a resist layer 14 provided with an opening 14a.

Figure 11A:
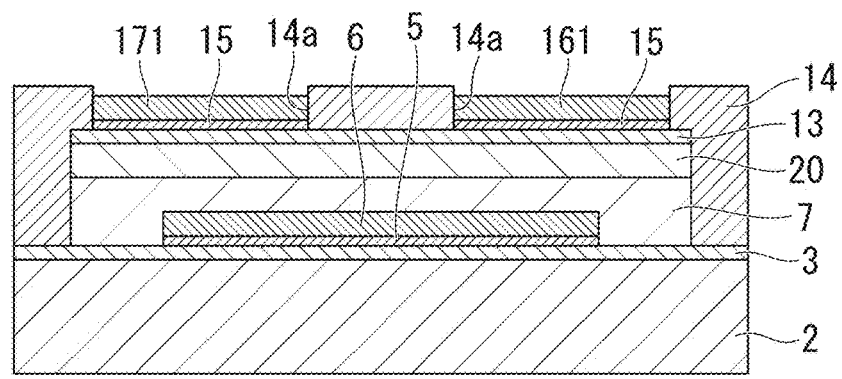
FIG. 11A is a process view showing the manufacturing method of the second embodiment.

Next, as shown in FIG. 11A, a colloidal solution of a divalent palladium salt is made to come into contact with the base film 13 exposed through the opening 14a, thereby capturing the catalyst 15 used in electroless plating to the surface of the base film 13. Thereafter, an electroless plating solution is made to come into contact with the catalyst 15, and thereby metal ions dissolved in the electroless plating solution is reduced and deposited on the surface of the catalyst 15, so as to selectively form a first electrode 161 and a third electrode 171 made of nickel phosphorus in the opening 14a (first electroless plating).

Figure 11B:
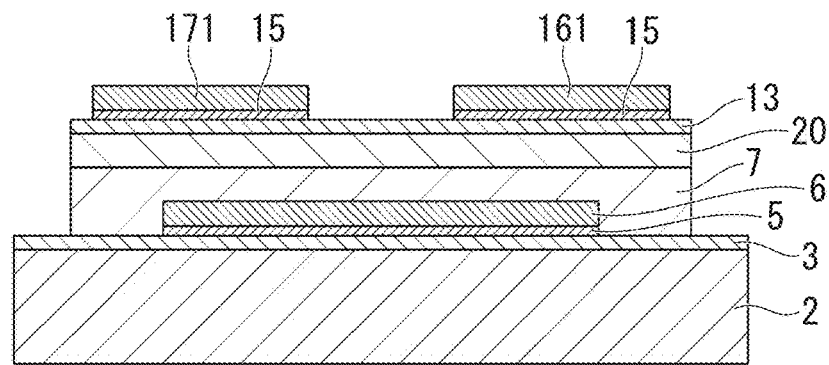
FIG. 11B is a process view showing the manufacturing method of the second embodiment.

Next, as shown in FIG. 11B, the entire surface of the remaining resist layer is exposed to ultraviolet, and then the resist layer is removed by a generally known developer. In this way, the first electrode 161 and the third electrode 171 are formed.

Figure 11C:
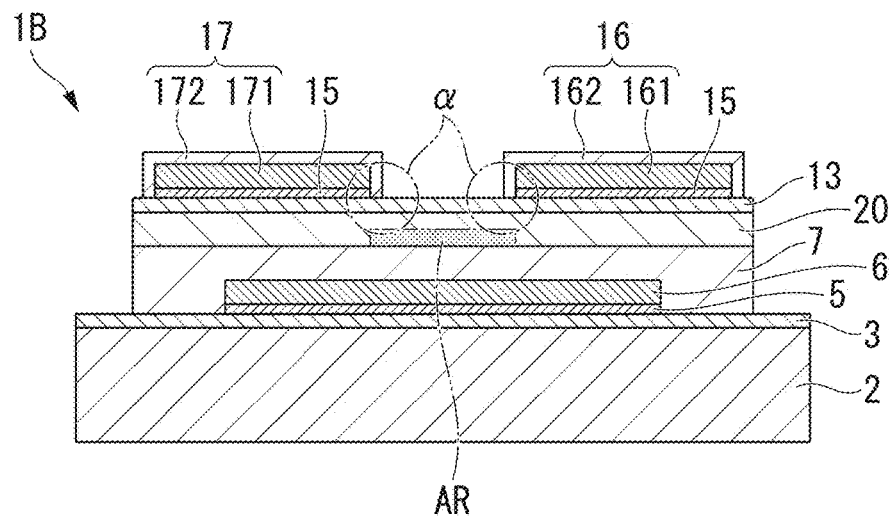
FIG. 11C is a process view showing the manufacturing method of the second embodiment.

Next, as shown in FIG. 11C, the entire body is immersed into a gold plating bath for substitution to allow the surface of the first electrode 161 and the third electrode 171 to be substituted and deposited with gold, and is further immersed into a gold plating bath for reduction to thereby form a second electrode 162 and a fourth electrode 172, which are plated with gold, on the surface of the first electrode 161 and the third electrode 171 (second electroless plating). In this way, a source electrode 16 and a drain electrode 17 are formed.

In this way, it is possible to manufacture the transistor 1B.

Even in this transistor 1B, since a curable composition capable of forming an insulator layer having both excellent insulation properties and excellent dielectric properties is used, it is possible to easily manufacture a high-performance transistor.

Further, the base films 3 and 13 are formed by using a silane coupling agent as a formation material, and are smooth films. Therefore, problems caused by the uneven shapes of the base films do not occur, and it is possible to easily manufacture a high-performance transistor.

Further, in the source electrode 16 of the transistor 1B, the second electrode 162 is formed using a metal material having a work function (energy level difference with HOMO of the semiconductor layer 20 is small) at which electron transfer is easier between the formation material of the semiconductor layer 20 and the second electrode 162 compared to between the first electrode 161 and the second electrode 162. In the drain electrode 17 of the transistor 1B, the fourth electrode 172 is formed using a metal material having a work function (energy level difference with HOMO of the semiconductor layer 20 is small) at which electron transfer is easier between the formation material of the semiconductor layer 20 and the fourth electrode 172 compared to between the third electrode 171 and the fourth electrode 172. In the enclosed position shown by a reference numeral α, electric current easily flows into the channel region AR from the second electrode 162 and the fourth electrode 172, and therefore it is possible to realize a high-performance transistor 1B.

Further, since the first electrode 161 is covered with the second electrode 162 and the third electrode 171 is covered with the fourth electrode 172, the temporal corrosion of the first electrode 161 and the third electrode 171 is suppressed, and there is also an advantage in that the performance of the transistor can be stably maintained.

The transistor of the present embodiment is configured such that the semiconductor layer 20 is not in contact directly with the source electrode 16 and the drain electrode 17 but is in contact with the source electrode 16 and the drain electrode 17 through the base film 13, but the base film 13 is formed in a very thin layer having a thickness of several nanometers (nm). Therefore, the effect of the base film 13 influencing transistor characteristics is small, and electric current flows well between the semiconductor layer 20 and the source electrode 16 and between the semiconductor layer 20 and the drain electrode 17.

Heretofore, an example of an embodiment of the present invention has been described with reference to the accompanying drawing, but the present invention is not limited to the example. The shapes, combination, and the like of the components described in the above-mentioned example are merely examples, and can be variously modified based on design requirements and the like without departing from the scope of the present invention.

For example, a substrate can be made of a non-metallic material. A plurality of plating members in each of which a base film is formed on a PET substrate (non-metallic substrate) are prepared. The plating members are conveyed, and simultaneously a transistor is manufactured using the above-mentioned manufacturing method in the conveying procedure. Thereby, it is possible to form a high-performance transistor on the PET substrate.

Moreover, in a roll to roll process, in which a plating member in which a base film is formed on a long PET film having flexibility, as a substrate, is rolled, the rolled plating member is conveyed while unrolling, transistors are continuously manufactured using the above-mentioned manufacturing method, and then the manufactured transistors are rolled, it is possible to form a transistor on the PET film.

In this case, when a curable composition containing the above-mentioned third organic compound (e) is used as the curable composition, it is possible to impart flexibility to the insulator layer to be formed, so that it is possible to form a transistor on a PET film in a roll to roll process while suppressing the damage to an insulator layer during manufacturing.

Further, in the present embodiment, a base film is formed using a silane coupling agent as a formation material, a catalyst for electroless plating is captured on the base film, and then electroless plating is performed, so as to form a gate electrode, a source electrode and a drain electrode. However, these electrodes may also be formed by forming any one or two electrodes of these electrodes using the above-mentioned method and forming the remaining electrodes using another method. For example, the gate electrode may be formed using a generally known patterning method, and the source electrode and drain electrode, which are formed in the same layer, may be formed using the above-mentioned manufacturing method.

Moreover, in the present embodiment, it has been described that a coating film, which was formed by applying a solution containing a curable composition, is selectively exposed to light through a mask, so as to form an insulator layer. However, the present invention is not limited thereto, and the entire coating film formed may be exposed to light to allow the entire coating film to be used as an insulator layer.

EXAMPLES

Hereinafter, the present invention will be described in more detail with reference to the following Examples, but the scope of the present invention is not limited to these Examples.

Example 1

In Example 1, the following liquid compositions were prepared, and the differences in physical properties between organic compounds were compared with each other.

(Liquid Composition 1)

(a) Organic compound: 6 mass % of tris(2,3-epoxypropyl) isocyanurate (379506, manufactured by Sigma-Aldrich, Inc.) represented by Formula (100) below (c) photocationic polymerization initiator: 0.5 mass % of (thiophenoxyphenyl)diphenylsulfonium hexafluorophosphate-bis(diphenylsulfonium)diphenylthioether hexafluorophosphate blend, 50% in propylene carbonate (OMPH076, manufactured by Gelest Corporation)

(d) 4 mass % of polyvinyl phenol (PVP) (436224, manufactured by Sigma-Aldrich, Inc.)

Solvent: 89.5 mass % of cyclohexanone+acetonitrile (cyclohexanone:acetonitrile=6:4)

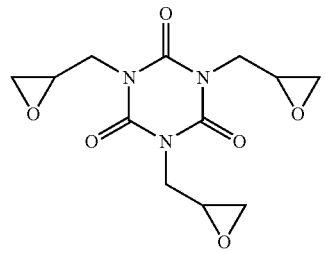

(100)

(Liquid Composition 2)

Liquid composition 2 was prepared in the same manner as liquid composition 1, except that tetraphenylol ethane glycidyl ether (412961, manufactured by Sigma-Aldrich, Inc.) was used as the organic compound (a), and only cyclohexane was used as the solvent.

(Liquid Composition 3)

Liquid composition 3 was prepared in the same manner as liquid composition 2, except that a bisphenol A epoxy monomer (RE-310s, manufactured by Nippon Kayaku Co., Ltd.) was used as the organic compound (a).

(Liquid Composition 4)

Liquid composition 4 was prepared in the same manner as liquid composition 2, except that trimethylol propane triglycidyl ether (430269, manufactured by Sigma-Aldrich Inc.) represented by Formula (101) below was used as the organic compound (a).

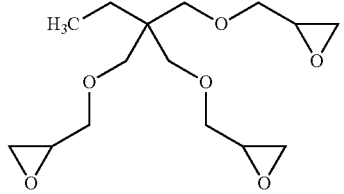

(101)

Figure 12A:
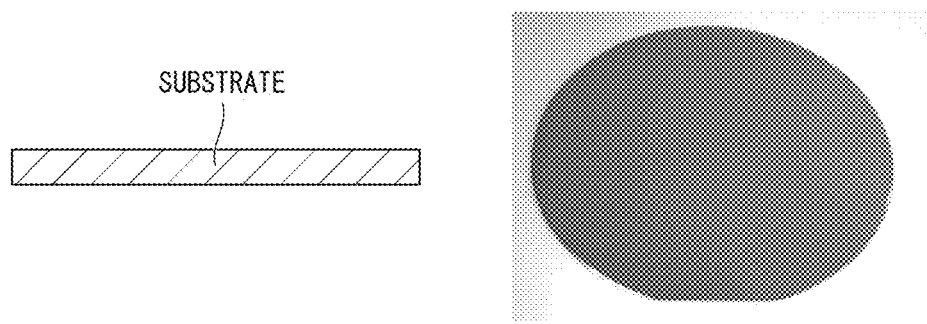
FIG. 12A is a view showing a process of manufacturing a sandwich cell evaluated in Example 1.
Figure 12B:
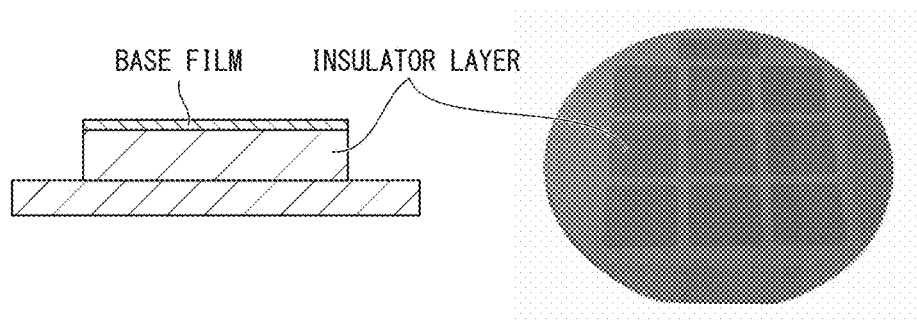
FIG. 12B is a view showing a process of manufacturing the sandwich cell evaluated in Example 1.
Figure 12C:
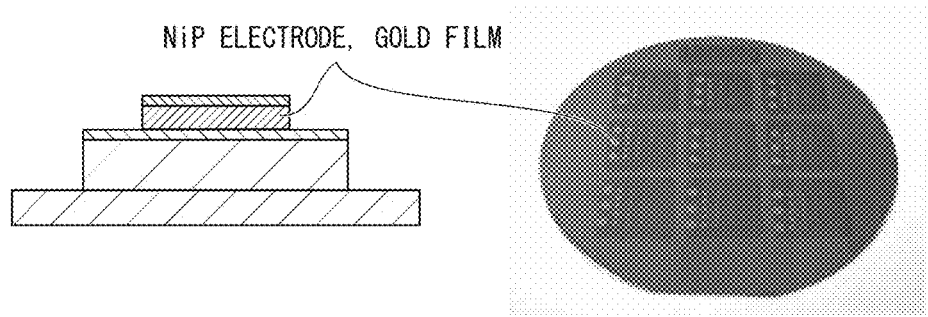
FIG. 12C is a view showing a process of manufacturing the sandwich cell evaluated in Example 1.

FIGS. 12A to 12C are views showing a process of manufacturing the sandwich cell evaluated in Example 1. Following the steps shown in FIGS. 12A to 12C, an insulator layer was formed using each of the above-mentioned liquid compositions to manufacture a sandwich cell.

First, an insulator layer and a base film were laminated (refer to FIG. 12B) on a silicon substrate (n-type abrasive product, 0.003 Ωcm, manufactured by Nakayama Semiconductor Co., Ltd.) (refer to FIG. 12A) by the following method.

Specifically, the liquid composition was applied onto the silicon substrate by spin coating (1000 rpm×30 seconds). Then, the substrate coated with the liquid composition was heated at 105° C. for 5 minutes to volatilize cyclohexanone (solvent), so as to form a coating film of a curable composition on the silicon substrate.

Next, the coating film was irradiated with i-line ray (365 nm) at an irradiation intensity of 700 mJ/cm$^2$ through a photomask, was further heated (post-baked) at 120° C. for 10 minutes, and then immersed in acetone for 1 minute to be developed, so as to form an insulator layer.

Figure 13:
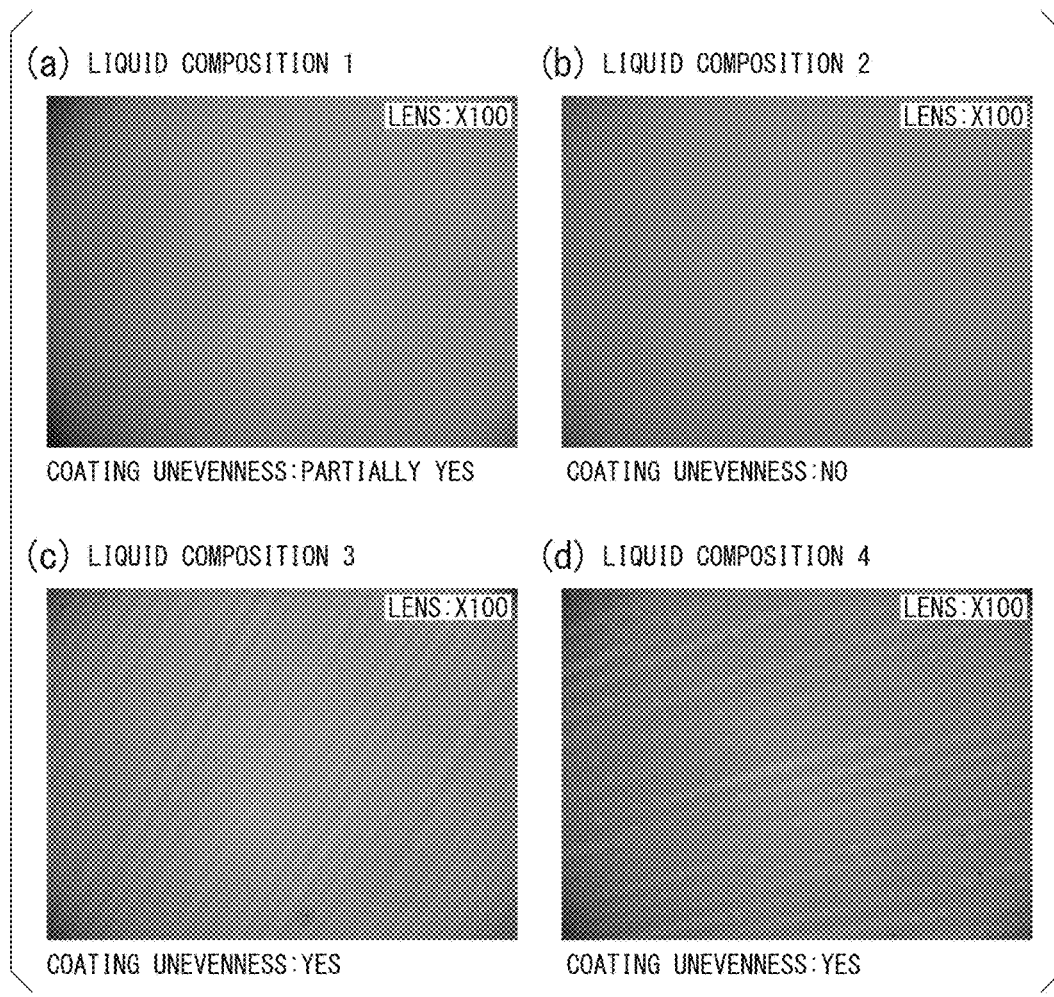
FIG. 13 shows photographs showing the results of Example 1.

FIG. 13 shows enlarged photographs of the surface of the formed insulator layer using an optical microscope. FIG. 13(a) shows the result using the liquid composition 1, FIG. 13(b) shows the result using the liquid composition 2, FIG. 13(c) shows the result using the liquid composition 3, and FIG. 13(d) shows the result using the liquid composition 4.

As shown in FIG. 13, the difference in the surface state of the formed insulator layers occurred depending on the organic compound species.

Specifically, as shown in FIGS. 13(c) and 13(d), streaky marks, seen as coating unevenness at the time of coating, were formed on the surface of each of the insulator layers using the liquid compositions 3 and 4. Further, although unclear in the photograph, as shown in FIG. 13(a), it was found that coating unevenness also occurred even on the surface of the insulator layer using the liquid composition 1, although this coating unevenness is small in comparison with those of the liquid compositions 3 and 4 that are used.

On the other hand, as shown in FIG. 13(b), coating unevenness did not occur on the surface of the insulator layer using the liquid composition 2 shown in FIG. 13(b), and an insulator layer having a flat surface was formed.

The surface of the formed insulator layer was cleaned with atmospheric-pressure oxygen plasma, and then a silane coupling agent, which is a formation material of a base film for electroless plating, was formed into a film. In the present Example, as the silane coupling agent, 3-aminopropyltriethoxysilane having a primary amino group (KBE-903, manufactured by Shin-Etsu Silicone Co., Ltd.) was used. The silane coupling agent was dissolved in methyl isobutyl ketone to have a content of 0.2 mass % to obtain a liquid product, and then the liquid product was applied onto the substrate by spin coating (4000 rpm×30 seconds). Thereafter, the substrate coated with the liquid product was heated at 120° C. for 5 minutes to volatilize methyl isobutyl ketone (solvent), so as to form a base film.

Next, as shown in FIG. 12C, an upper electrode (NiP electrode, gold film) was formed on the base film, so as to fabricate a sandwich cell.

Specifically, a photoresist (SUMIRESIST PFI-34A, manufactured by Sumitomo Chemical Co., Ltd.) was applied to the surface of the base film coated with HMDS by spin coating (1000 rpm×30 seconds), and heated at 90° C. for 5 minutes, so as to form a resist layer.

Next, the resist layer was irradiated with light emitted from a low-pressure mercury lamp through a quartz photomask for 5 minutes, heated (post-baked) at 110° C. for 5 minutes, and then immersed into 2.38 mass % of an aqueous TMAH solution for 90 seconds to thereby develop the resist layer, so as to form an opening in the resist layer.

Next, the substrate provided with the resist layer having the opening was washed with water at room temperature for 30 seconds, and then immersed into a catalyst colloid solution for electroless plating (Melplate activator 7331, manufactured by Meltex Corporation) at room temperature for 60 seconds, so as to adhere a catalyst to the base film exposed through the opening of the resist layer.

Next, the surface of the base film was washed with water, and then immersed into an electroless plating solution (Melplate NI-867, manufactured by Meltex Corporation) at 70° C. for 180 seconds to deposit nickel phosphorus on the catalyst adhered to the opening of the resist layer, so as to perform nickel-phosphorus plating.

Next, the surface of the nickel-phosphorus plated portion (NiP electrode) was washed with water, and then immersed into a gold plating bath for substitution for 1 minute and further immersed into a plating bath for reduction for 3 minutes to thereby perform electroless plating on the upper surface of the NiP electrode and coat the upper surface of the NiP electrode with gold, so as to fabricate an upper electrode.

Next, the surface of the upper electrode was water-washed and then dried. Then, the entire surface including the remaining resist layer was irradiated with i-line ray at an irradiation intensity of 300 mJ/cm$^2$, and then immersed into 2.38 mass % of an aqueous TMAH solution to remove the resist layer. The resulting product was water-washed and dried to thereby fabricate a sandwich cell.

The dielectric constant and insulation characteristics of the insulator layer were measured using the fabricated sandwich cell by the following method.

(Dielectric Constant)

The measurement of capacitance of the fabricated insulator layer was performed in a frequency range of 100 Hz to 1 MHz using an LCR meter (4284A, manufactured by Agilent Technologies).

Figure 14:
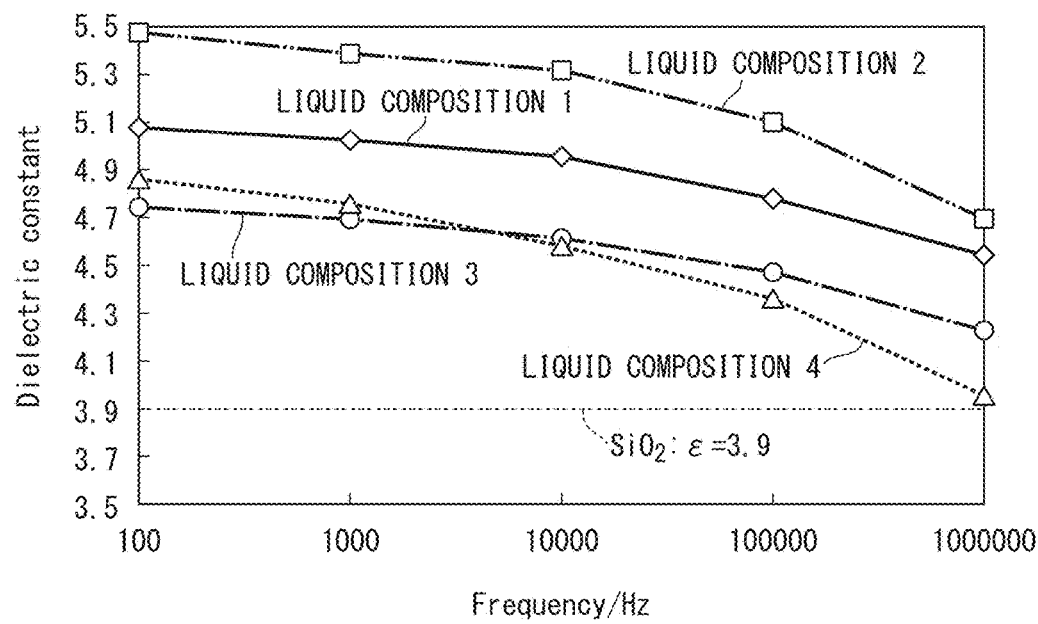
FIG. 14 is a graph showing the frequency dependence of dielectric constant of an insulator layer of Example 1.

FIG. 14 is a graph showing the frequency dependency of dielectric constant calculated from capacitance of the insulator layer of the fabricated sandwich cell. In the graph of FIG. 14, the horizontal axis indicates the measurement frequency (unit: Hz), and the vertical axis indicates the measured dielectric constant.

It was found that each of the insulator layers fabricated in Example 1 had a high dielectric constant greater than $\varepsilon=3.9$, which is a dielectric constant of a $SiO_2$ thermal oxide film (generally known inorganic insulator), with respect to any measurement frequency. It was found that, among these liquid compositions, when the liquid composition 2 combined with tetraphenylol ethane glycidyl ether was used, an insulator layer having a high dielectric constant was obtained.

(Insulating Characteristics)

In the evaluation of insulating characteristics of the fabricated insulator layer, current density was measured using the Semiconductor Characterization System (4200-SCS, manufactured by KEITHLEY Co., Ltd.) when a voltage of 0 MV/cm to 2 MV/cm was applied.

Figure 15:
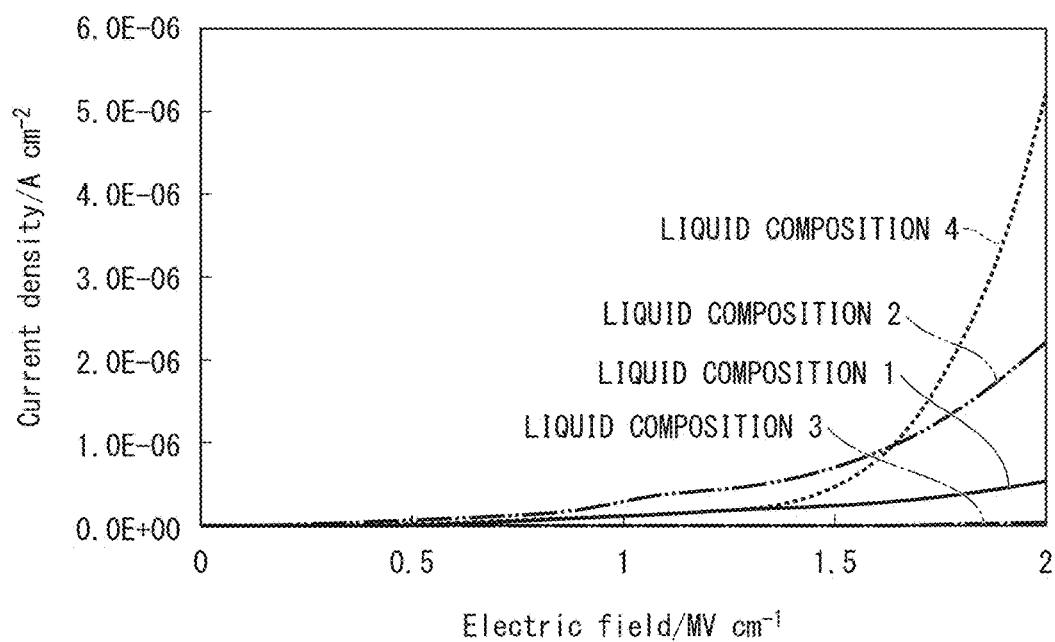
FIG. 15 is a graph showing the evaluation results of insulating properties of the insulator layer of Example 1.

FIG. 15 is a graph showing the evaluation results of insulating characteristics of the insulator layer of the fabricated sandwich cell. In the graph of FIG. 15, the horizontal axis indicates the measurement voltage (unit: MV/cm), and the vertical axis indicates the measured current density (A/cm$^2$).

As the results of evaluation, it was found that, when the liquid composition 3 combined with a bisphenol A epoxy monomer was used, an insulator layer having high insulating properties was obtained.

Example 2

In Example 2, raw material solutions were prepared according to the combination ratios of the following (a) to (d) and the solvent shown in Table 1 below, and the differences in physical properties of the prepared raw material solutions were compared.

(a) First organic compound: tetraphenylol ethane glycidyl ether (b) Second organic compound: bisphenol A epoxy monomer (c) Photocationic polymerization initiator: OMPH076 (manufactured by Gelest Inc.)

(d) Polyvinyl phenol

Solvent: cyclohexanone

TABLE 1

|  | Polyvinyl phenol (mass %) | First organic compound (mass %) | Second organic compound (mass %) | Photocationic polymerization initiator (mass %) | Solvent (mass %) |
|---|---|---|---|---|---|
| Raw material solution 1 | 4 | 5 | 1 | 0.5 | 89.5 |
| Raw material solution 2 |  | 3 | 3 |  |  |
| Raw material solution 3 | 2 | 7 | 1 |  |  |
| Raw material solution 4 |  | 5 | 3 |  |  |
| Raw material solution 5 | 0 | 9 | 1 |  |  |
| Raw material solution 6 |  | 7 | 3 |  |  |

The sandwich cell was fabricated using each of the above-mentioned raw material solutions in the same manner as in Example 1, and the dielectric constant and insulation characteristics of the formed insulator layer were measured.

FIG. 16 shows enlarged photographs of the surface of the formed insulator layer using an optical microscope. FIG. 16(a) shows the result using the raw material solution 1, and, similarly below, one of FIGS. 16(b) to 16(f) shows the result using each of the raw material solutions 2 to 6.

As shown in FIG. 16, the difference in the surface state of the formed insulator layers occurred depending on the combination ratio of the organic compounds. Specifically, as shown in FIGS. 16(d) and 16(f), streaky marks, seen as coating unevenness at the time of coating, were formed on the surface of each of the insulator layers using the raw material solutions 4 and 6. On the other hand, as shown in FIGS. 16(a) to 16(c) and 16(e), coating unevenness did not occur on the surface of each of the insulator layers using the raw material solutions 1 to 3 and 5, and insulator layers having a flat surface were formed.

Figure 17:
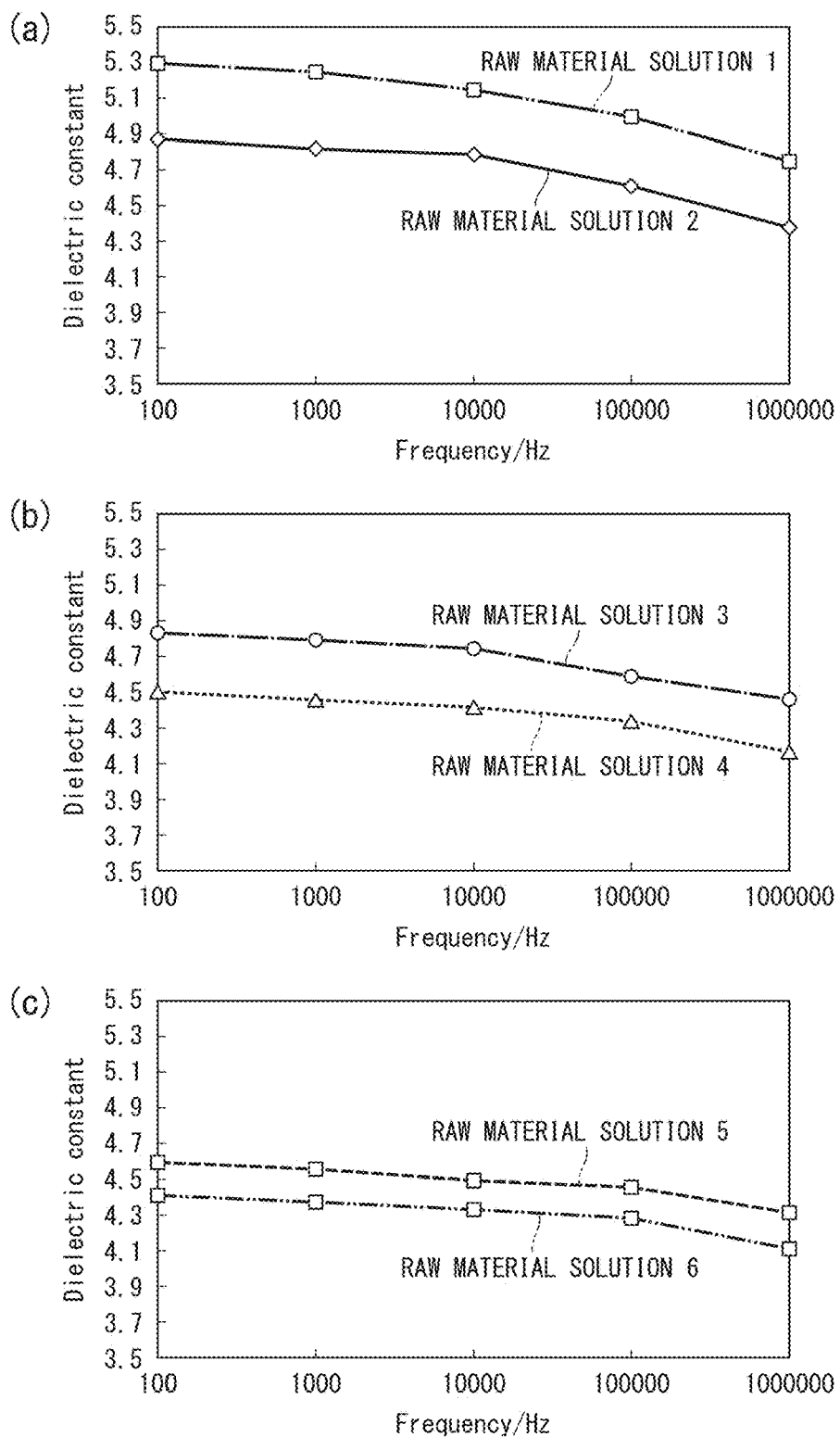
FIG. 17 shows graphs showing the frequency dependence of dielectric constant of an insulator layer of Example 2.

FIG. 17 shows graphs showing the frequency dependency of dielectric constant calculated from capacitance of each of the insulator layers of the fabricated sandwich cell. FIG. 17(a) shows the result of the raw material solution containing 4 mass % of PVP to the total raw material solution, FIG. 17(b) shows the result of the raw material solution containing 2 mass % of PVP to the total raw material solution, and FIG. 17(c) shows the result of the raw material solution containing no PVP. In the graphs of FIG. 17, the horizontal axis and the vertical axis are the same as the horizontal axis and the vertical axis in FIG. 14.

It was found that each of the insulator layers fabricated in Example 2 had a high dielectric constant greater than ε=3.9, which is a dielectric constant of a SiO2 thermal oxide film (generally known inorganic insulator), with respect to any measurement frequency. Further, it was found that, in any combination, when the amount of tetraphenylol ethane glycidyl ether to the constant amount of the organic compound is increased, the dielectric constant of the insulator layer to be obtained becomes larger.

(Insulating Characteristics)

Figure 18:
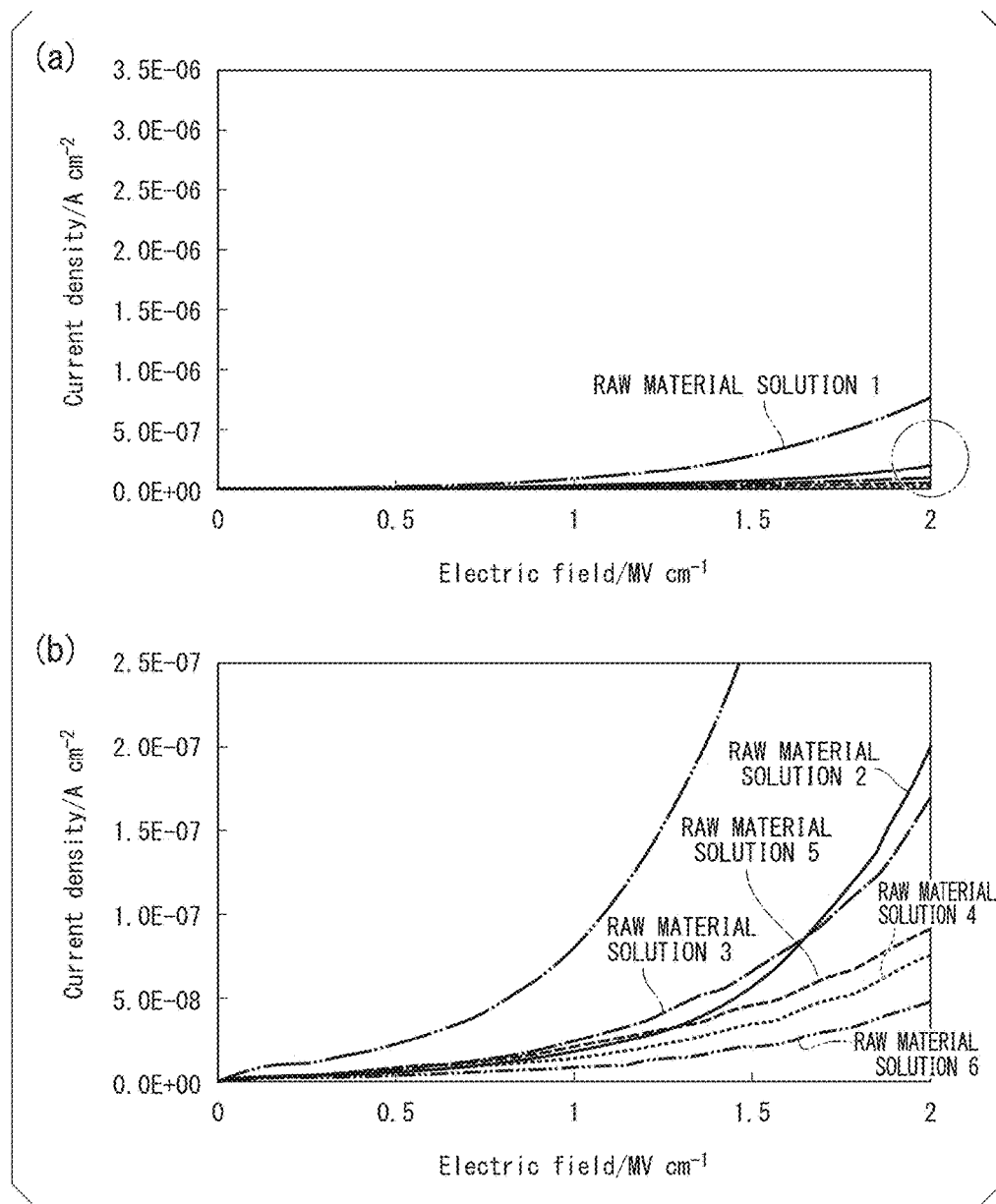
FIG. 18 shows graphs showing the evaluation results of insulating properties of an insulator layer of Example 2.

FIG. 18 shows graphs showing the evaluation results of insulating characteristics of each of the insulator layers of the fabricated sandwich cell. FIG. 18 (a) is an overall view, and FIG. 18 (b) is a partially enlarged view. In the graphs of FIG. 18, the horizontal axis indicates the measurement voltage (unit: MV/cm), and the vertical axis indicates the measured current density (A/cm$^2$).

As the results of evaluation, it was found that, when each of the raw material solutions was combined with a bisphenol A epoxy monomer, insulating properties were greatly improved, and insulator layers having high insulating properties were obtained.

From the above results, it was found that, when tetraphenylol ethane glycidyl ether and a bisphenol A epoxy monomer were used in combination with each other as organic compounds, it was possible to form an insulator having both excellent insulating properties and excellent dielectric properties without one of the tetraphenylol ethane glycidyl ether and the bisphenol A epoxy monomer deteriorating excellent physical properties of the other of the tetraphenylol ethane glycidyl ether and the bisphenol A epoxy monomer.

Example 3

(Fabrication of Gate Electrode)

In Example 3, 3-aminopropyltriethoxysilane (KBE903, manufactured by Shin-Etsu Silicone Co., Ltd.), which is an amine-based silane coupling agent, was dissolved in methyl isobutyl ketone (hereinafter, sometimes referred to as MIBK) to have 0.2 mass % to prepare a liquid product, and this liquid product was used in forming a base film.

The surface of a PET substrate (Model number: A-4100 (no coat), manufactured by Toyobo Co., Ltd.) was cleaned with atmospheric-pressure oxygen plasma, and then a liquid product containing the amine-based silane coupling agent was applied onto the PET substrate by spin coating (4000 rpm×30 seconds). Thereafter, the PET substrate coated with the liquid product was heated at 120° C. for 10 minutes, so as to form a base film.

Next, a resist material (SUMIRESIST PFI-34A6, manufactured by Sumitomo Chemical Co., Ltd.) was applied to the surface of the substrate provided with the base film by spin coating, and then heated (prebaked) at 90° C. for 5 minutes, so as to form a resist layer. The spin coating was performed under a condition of 1000 rpm and 30 seconds, and a resist layer having a thickness of about 1 μm was formed.

Next, the resist layer was exposed with ultraviolet having an intensity of 25 mW/cm$^2$ through a photomask for 5 seconds, heated (post-baked) at 120° C. for 5 minutes, and then immersed into 2.38 mass % of an aqueous TMAH solution for 2 minutes to thereby develop a mask pattern on the resist layer, so as to form an opening.

Next, the substrate provided with the resist layer having the opening was ultrasonically water-washed at room temperature for 30 seconds, and then immersed into a catalyst colloid solution for electroless plating (Melplate activator 7331, manufactured by Meltex Corporation) at room temperature for 60 seconds, so as to adhere a catalyst (Pd metal) to the base film exposed through the opening of the resist layer.

Next, the surface of the base film was washed with water, and then immersed into an electroless plating solution (Melplate NI-867, manufactured by Meltex Corporation) at 73° C. for 60 seconds to deposit nickel phosphorus on the catalyst adhered to the opening of the resist layer, so as to perform nickel-phosphorus plating.

Next, the surface of the resulting product was water-washed and then dried. Then, the entire surface including the remaining resist layer was exposed to ultraviolet having an intensity of 25 mW/cm$^2$ for 1 minute, and then immersed into ethanol for 1 minute to thereby remove the resist layer, so as to fabricate a gate electrode.

Figure 19:
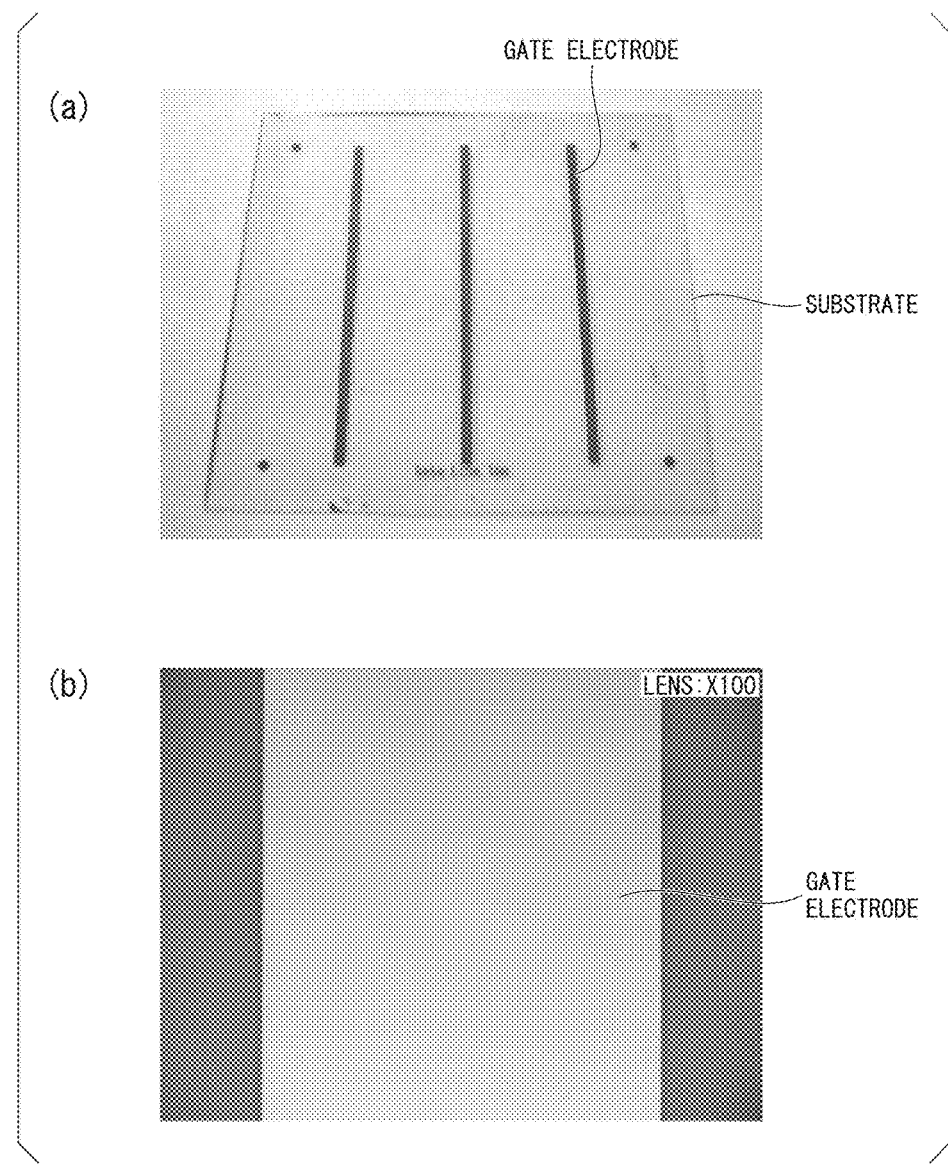
FIG. 19 shows photographs showing the results of Example 3.

FIG. 19 shows photographs of the gate electrode. FIG. 19 (*a*) is an overall photograph of the substrate provided with the gate electrode. FIG. 19 (*b*) is an enlarged photograph of the gate electrode using an optical microscope. From FIG. 19, it is found that a slightly uneven flat gate electrode is formed.

(Fabrication of Insulator Layer)

In order to improve the adhesiveness between the gate electrode and the insulator layer to be formed, the substrate provided with the gate electrode was immersed into an aqueous NaOH solution of 50 g/L, and a degreasing process of the surface was performed.

Next, the degreased substrate provided with the gate electrode was heated at 120° C. for 10 minutes to be dried, and then the surface of the substrate provided with the gate electrode was treated using atmospheric-pressure oxygen plasma. Thereafter, each of the raw material solutions 1 to 6 of Example 2 was applied onto the plasma-treated surface by spin coating (1500 rpm×30 seconds). Then, the resulting product was heated at 105° C. for 5 minutes to volatilize cyclohexane (solvent), so as to form a coating film of a curable composition.

Next, the coating film was irradiated with ultraviolet for 20 seconds through a mask having an opening in the portion forming an insulator layer. In order to accelerate curing, the ultraviolet-irradiated coating film was heated at 120° C. for 10 minutes, and then immersed into acetone for 1 minute to form a patterned film. Then, the patterned film was heat-treated at 120° C. for 30 minutes to form an insulator layer.

Figure 20:
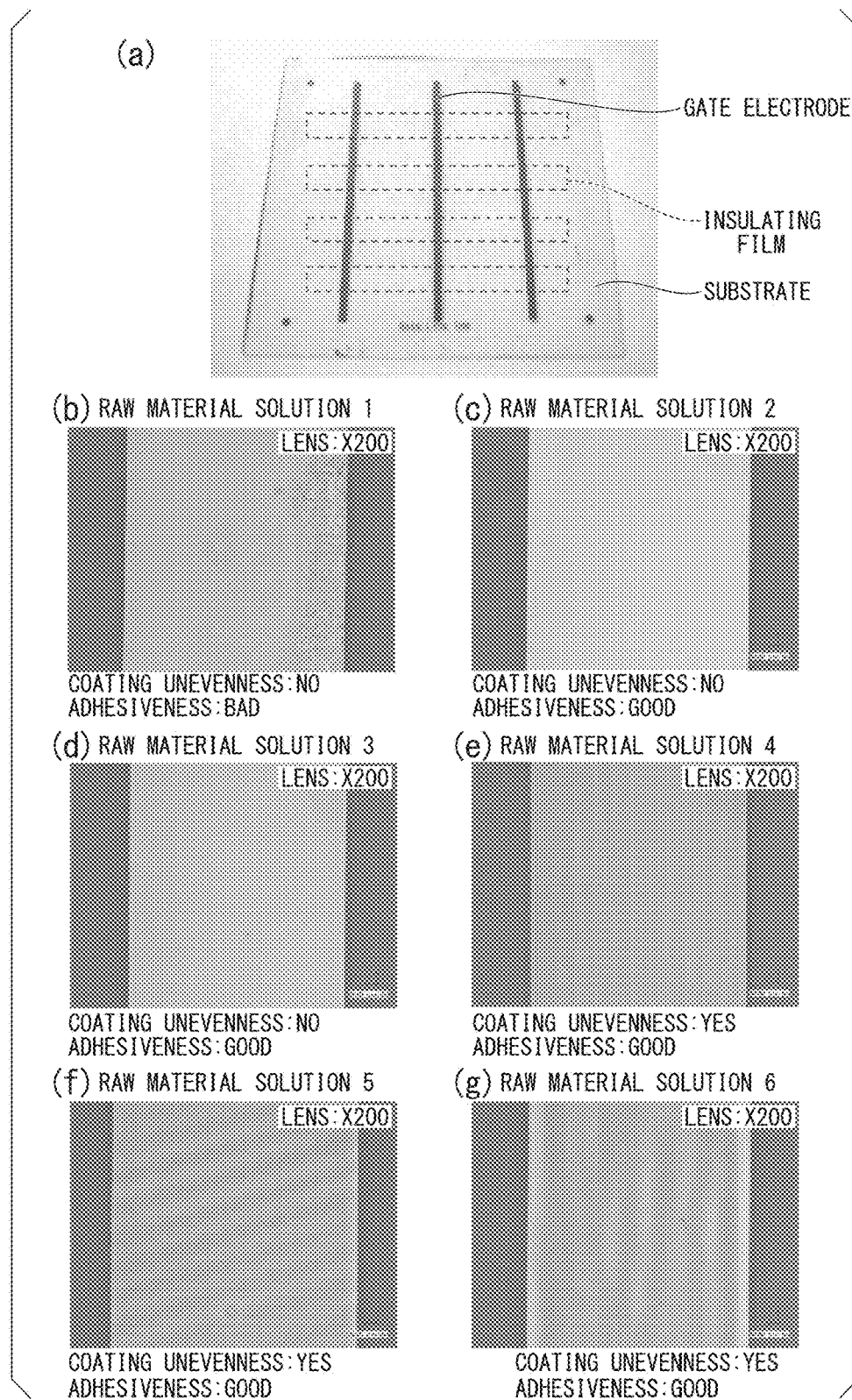
FIG. 20 shows photographs showing the results of Example 3.

FIG. 20 is a photograph of the insulator layer. FIG. 20 (*a*) is a representative photograph of the substrate provided with the insulator layer, and FIG. 20 (*b*) is an enlarged photograph of the region surrounded by a dash line of FIG. 20 (*a*) with respect to the insulator layer using the raw material solution 1. Similarly below, one of FIGS. 20 (*c*) to 20 (*g*) is an enlarged photograph of the insulator layer of the region surrounded by the dash line of FIG. 20 (*a*) with respect to the insulator layer using each of the raw material solutions 2 to 6.

As the results of observation, as shown in FIGS. 20(*e*) to 20(*g*), streaky marks, seen as coating unevenness at the time of coating, were formed on the surface of each of the insulator layers using the raw material solutions 4 to 6. On the other hand, as shown in FIGS. 20(*a*) to 20(*c*), coating unevenness did not occur on the surface of each of the insulator layers using the raw material solutions 1 to 3, and insulator layers having a flat surface were formed. However, in the insulator layer using the raw material solution 1, the adhesiveness between the insulator layer and the gate electrode was low, and partial stripping was observed.

(Fabrication of Source and Drain Electrodes)

Next, the fabrication and electroless plating of the base film and the resist layer were performed on the entire surface of the side where the insulator layer is formed on the PET substrate in the same manner as the above-mentioned process (fabrication of the gate electrode), so as to form a patterned NiP electrode on the insulator layer. The NiP electrode corresponds to the first electrode and the third electrode described in the embodiment.

In addition, after stripping the resist, the NiP electrode was immersed into a gold plating bath for substitution for 1 minute and further immersed into a plating bath for reduction for 3 minutes to thereby perform electroless plating to coat the surface of the NiP electrode with gold, so as to fabricate a source electrode and a drain electrode. The gold film coating the surface of the NiP electrode corresponds to the second electrode and the fourth electrode described in the embodiment.

FIG. 21 shows the photographs of the source electrode and the drain electrode. FIG. 21 (*a*) is a representative photograph of the substrate provided with the source electrode and the drain electrode, and FIG. 21 (*b*) is an enlarged photograph of the source electrode and the drain electrode formed on the insulator layer using the raw material solution 2. Similarly below, one of FIGS. 21 (*c*) to 21 (*f*) is an enlarged photograph of the source electrode and the drain electrode formed on the insulator layer using each of the raw material solutions 3 to 6.

As the results of observation, in the surface of the insulator layer, it was confirmed that a good source electrode and a good drain electrode were formed. Further, damage to the insulator layer in the electroless plating process was not confirmed.

(Fabrication of Organic Semiconductor Layer)

A toluene solution of 6,13-bis(triisopropylsilylethynyl) pentacene (TIPS pentacene) (716006, manufactured by Sigma-Aldrich, Inc.) was dropped between the source electrode and the drain electrode under a nitrogen atmosphere, and naturally dried to thereby form a semiconductor layer, so as to fabricate a transistor. Here, the adjustment of the TIPS pentacene/toluene solution used was also performed under a nitrogen atmosphere.

Figure 22:
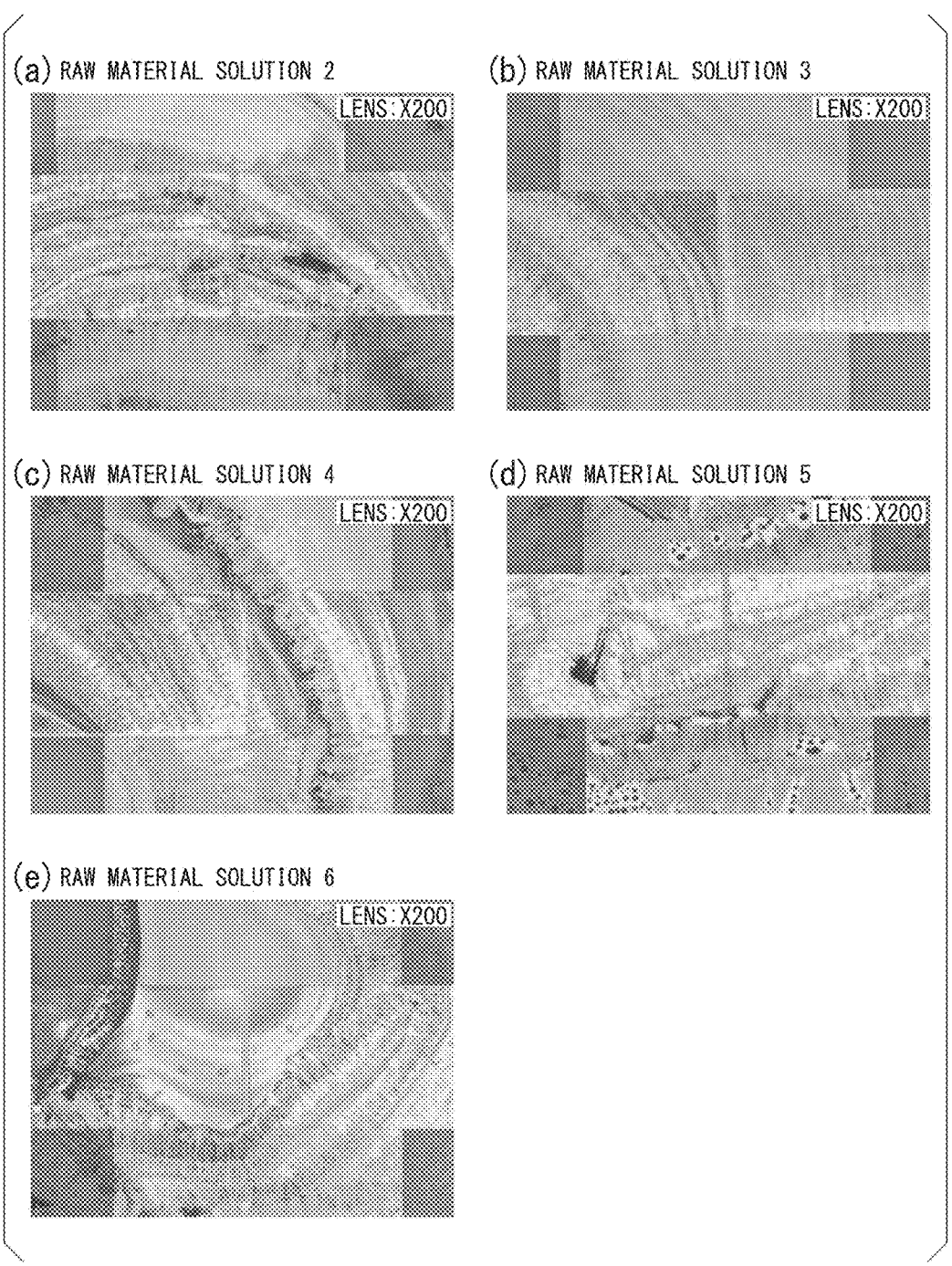
FIG. 22 shows photographs showing the results of Example 3.

FIG. 22 shows enlarged photographs of the source electrode and the drain electrode having the surface provided with the organic semiconductor layer. FIGS. 22 (*a*) to 22 (*e*) are enlarged photographs of the source electrode and the drain electrode formed on the insulator layers using the raw material solutions 2 to 6.

As shown in FIG. 22, it was observed that crystals of TIPS pentacene were formed between the source electrode and the drain electrode.

(Evaluation of Transistor)

The transistor characteristics of the fabricated transistor were evaluated using the Semiconductor Characterization System (4200-SCS, manufactured by KEITHLEY Co., Ltd.).

Figure 23:
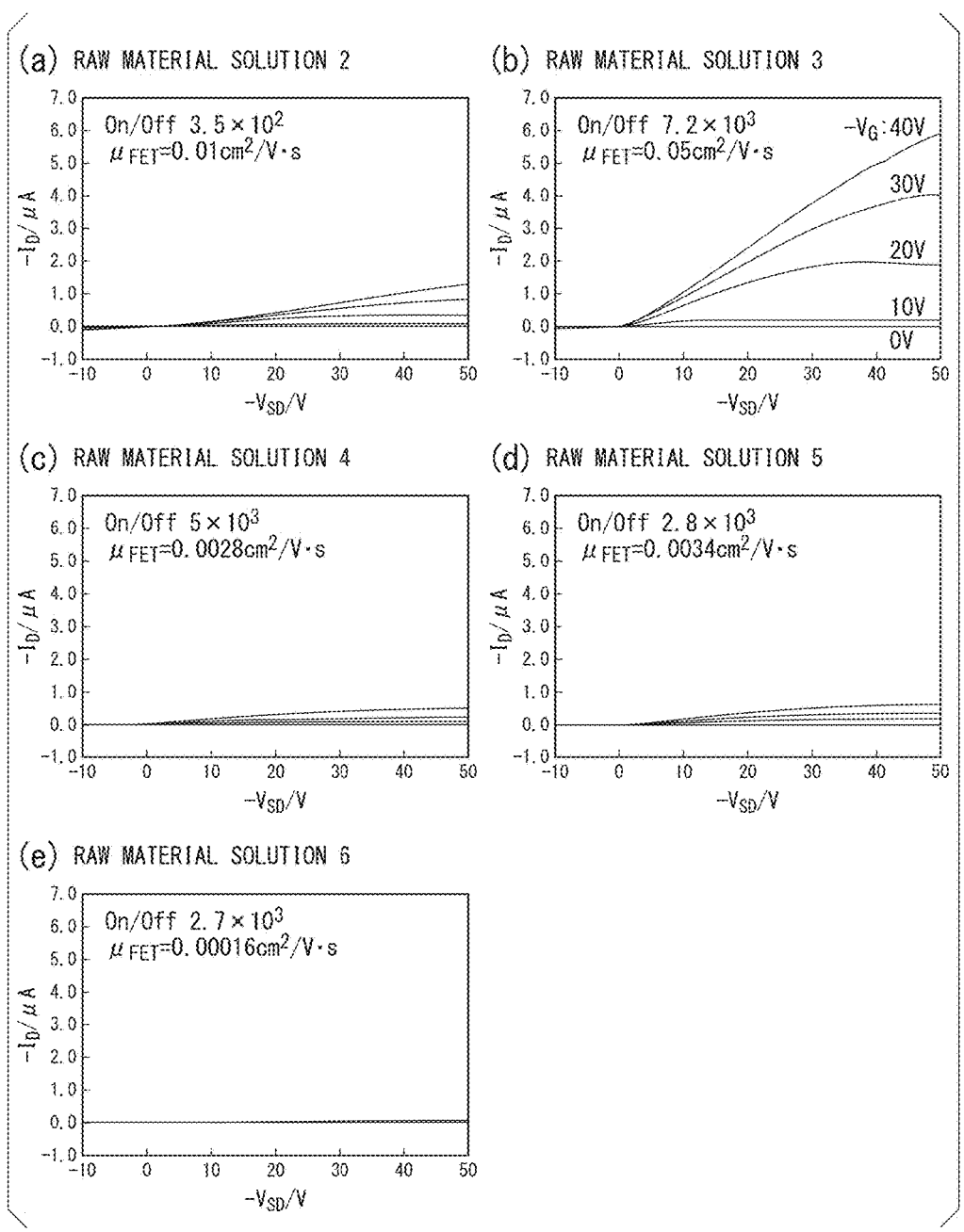
FIG. 23 shows graphs showing the results of Example 3.

FIG. 23 shows graphs showing the transistor characteristics of the transistor fabricated by a wet process using the above-mentioned method, and one of FIGS. 23(*a*) to 23(*e*) is a graph showing the transistor characteristics of the transistor provided with the insulator layer using each of the raw material solutions 2 to 6.

In each of the graphs of FIG. 23, in order to easily see the Figure, the gate voltage ($V_G$) of true value, which is a negative value, is multiplied by $-1$, and thereby is expressed as a positive value. With respect to the true value of the gate voltage, the positive value (a value corresponding to the gate voltage) used in the notation is expressed by "$-V_G$".

Similarly, the voltage ($V_{SD}$) between the source electrode and the drain electrode is expressed by using a value "$-V_{SD}$" as the corresponding positive value.

Further, the current value detected by the drain electrode to be measured is also expressed by using a value "$-I_D$" as the corresponding positive value.

In each of graphs of FIG. 23, the horizontal axis indicates a voltage applied between the source electrode and the drain electrode, and the vertical axis indicates a current value detected by a drain electrode. One of the plurality of results shown in FIG. 23 corresponds to each of the gate voltages applied to a gate electrode.

A gate voltage of 0 V to −40 V was applied to the gate electrode of the obtained organic thin film transistor, and a voltage of 0 V to −50 V was applied between source and drain to flow electric current. As a result, as shown in FIG. 23, holes are induced in the channel region (between source and drain) of a semiconductor layer, and the fabricated transistor was operated as a p-type transistor. Further, as shown in FIG. 23 (b), the transistor using the raw material solution 3 exhibited the best characteristics (mobility: 0.05 cm$^2$/Vs, On/Off ratio: 7.2×10$^3$).

Example 4

In Example 4, raw material solutions were prepared according to the combination ratios of the following (a) to (e) and the solvent shown in Table 2 below, and the differences in physical properties of the prepared raw material solutions were compared.

(a) First organic compound: tetraphenylol ethane glycidyl ether (b) Second organic compound: bisphenol A epoxy monomer (c) Photocationic polymerization initiator: triarylsulfonium hexafluoroantimonate mixture, 50% in propylene carbonate (654027, manufactured by Sigma-Aldrich Inc.)

(d) Polyvinyl phenol (e) Third organic compound: tris(4-hydroxyphenyl) methane triglycidyl ether (413305, manufactured by Sigma-Aldrich Inc.)

Solvent: cyclohexanone

TABLE 2

| | Polyvinyl phenol (mass %) | First organic compound (mass %) | Second organic compound (mass %) | Third organic compound (mass %) | Photocationic polymerization initiator (mass %) | Solvent (mass %) |
|---|---|---|---|---|---|---|
| Raw material solution 7 | 2 | 7 | 1 | 0 | 0.5 | 89.5 |
| Raw material solution 8 | | 5 | | 2 | | |

The first organic compound (a) used has a melting point of about 80° C., and is a flaky solid having high crystallinity at room temperature. On the other hand, the third organic compound (e) is an amorphous solid having a melting point of about 50° C.

The sandwich cell was fabricated using each of the above-mentioned raw material solutions according to the following method, and the dielectric constant and insulation characteristics of the formed insulator layer were measured.

First, the raw material solution 7 or 8 was applied onto a silicon substrate by dip coating film formation (lifting speed: 1 mm/s). Then, the substrate coated with the raw material solution was heated at 105° C. for 5 minutes to volatilize cyclohexanone (solvent), so as to form a coating film of a curable composition on the silicon substrate.

Next, the coating film was irradiated with i-line ray (365 nm) through a photomask at an irradiation intensity of 700 mJ/cm$^2$, further heated (post-baked) at 105° C. for 60 minutes, and then immersed into acetone for 1 minute to be developed, so as to form an insulator layer.

The surface of the formed insulator layer was cleaned with atmospheric-pressure oxygen plasma, and then a base film was formed using the liquid product of a silane coupling agent having the same composition as in Example 1. Specifically, the liquid product was applied by dip coating film formation (lifting speed: 1 mm/s), and then heated at 105° C. for 5 minutes to volatilize methyl isobutyl ketone (solvent), so as to form a base film.

Next, a photoresist was applied to the surface of the base film by spin coating (1000 rpm×30 seconds), and heated at 105° C. for 15 minutes, so as to form a resist layer.

Next, the resist layer was irradiated with light emitted from a low-pressure mercury lamp through a quartz photomask for 5 minutes, heated (post-baked) at 105° C. for 15 minutes, and then immersed into 2.38 mass % of an aqueous TMAH solution for 90 seconds to thereby develop the resist layer, so as to form an opening in the resist layer.

Next, in the same manner as in Example 1, a catalyst is adhered to the base film exposed through the opening of the resist layer. The surface of the base film was washed with water, and then immersed into an electroless plating solution at 70° C. for 120 seconds to deposit nickel phosphorus on the catalyst adhered to the opening of the resist layer, so as to perform nickel-phosphorus plating.

Next, the surface of the nickel-phosphorus plated portion (NiP electrode) was washed with water, and then immersed into a gold plating bath for substitution for 1 minute and further immersed into a plating bath for reduction for 3 minutes to thereby perform electroless gold plating on the upper surface of the NiP electrode and coat the upper surface of the NiP electrode with gold, so as to fabricate an upper electrode.

Next, the surface of the upper electrode was water-washed and then dried. Then, the entire surface including the remaining resist layer was irradiated with i-line ray at an irradiation intensity of 300 mJ/cm$^2$, and then immersed into 2.38 mass % of an aqueous TMAH solution to remove the resist layer. The resulting product was water-washed and dried to thereby fabricate a sandwich cell.

The surface observation and mechanical characteristics measurement of the fabricated insulator layer were performed, and the dielectric constant and insulating characteristics of the insulator layer were measured using the fabricated sandwich cell.

(Surface Observation)

As the result of observing the surface of each of the formed insulator layers with an optical microscope, it was found that coating unevenness was not observed even on the surface of any of the layers, and the surface was very flat. Further, as the result of measuring the surface roughness with a surface step meter (P-2, manufactured by TENCOR Corporation), the arithmetic average roughness (Ra) of the surface of the insulator layer fabricated using the raw material solution 7 was 18.4 Å, and the arithmetic average roughness (Ra) of the surface of the insulator layer fabricated using the raw material solution 8 was 11.5 Å. That is, the surface of the insulator layer fabricated using the raw material solution 8 was flat compared to the surface of the insulator layer fabricated using the raw material solution 7.

(Mechanical Characteristics)

The mechanical characteristics (hardness, Young's modulus) of each of the formed insulator layers was evaluated using a nanoindenter (triboindenter TI-950, manufactured by Hysitron Inc.) according to a nanoindentation technique. Measurements were performed three times with respect to each insulator layer, and arithmetic mean value of three times was calculated. The results are given in Table 3 below.

TABLE 3

| Sample name | | Raw material solution 7 | Raw material solution 8 |
|---|---|---|---|
| Hardness (GPa) | n1 | 0.318 | 0.294 |
| | n2 | 0.318 | 0.293 |
| | n3 | 0.317 | 0.293 |
| | Mean value | 0.318 | 0.293 |
| Young's modulus (Gpa) | n1 | 3.75 | 3.04 |
| | n2 | 3.78 | 3.09 |
| | n3 | 3.76 | 3.06 |
| | Mean value | 3.76 | 3.07 |

As the result of measurement, it was found that, when the raw material solution contained the third organic compound, the insulator layer was softened, and Young's modulus was lowered.

(Dielectric Constant)

Figure 24:
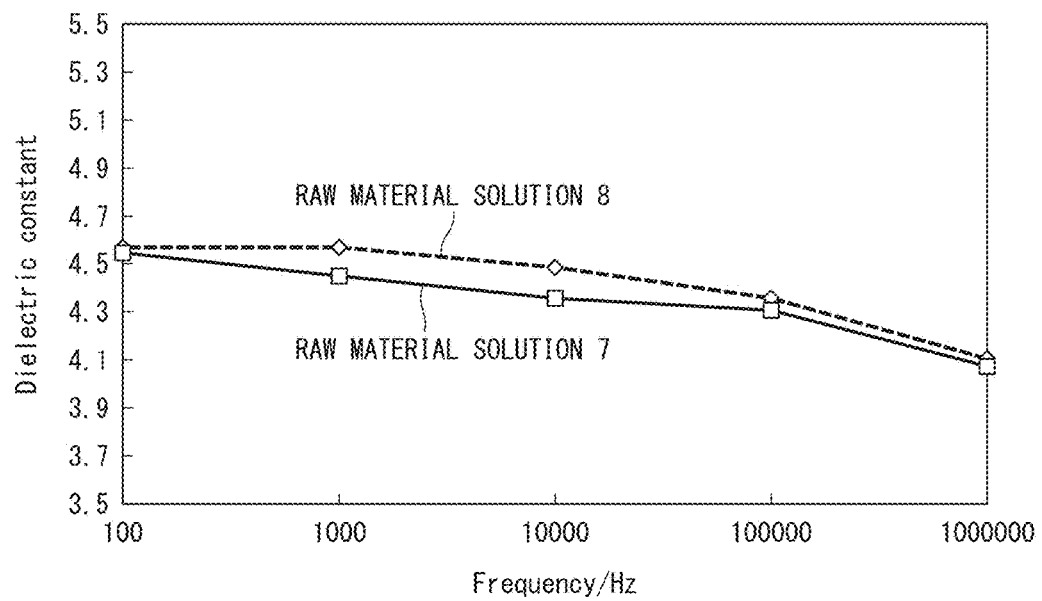
FIG. 24 is a graph showing the frequency dependence of dielectric constant of an insulator layer of Example 4.

The measurement of capacitance of the fabricated insulator layer was performed in the same manner as in Example 1. FIG. 24 is a graph showing the frequency dependency of dielectric constant calculated from capacitance of the insulator layer of the fabricated sandwich cell in Example 4. The graph of FIG. 24 corresponds to the graph of FIG. 14.

As the result of measurement, it was found that the insulator layer fabricated using any of the raw material solutions 7 and 8 also exhibited a high dielectric constant greater than $\varepsilon=3.9$, which is a dielectric constant of a $SiO_2$ thermal oxide film (generally known inorganic insulator). Therefore, it was found that, when the third organic compound was used, it was possible to soften the insulator layer without deteriorating the dielectric constant.

(Insulating Characteristics)

In the evaluation of insulating characteristics of the fabricated insulator layer, current density was measured using the Semiconductor Characterization System (4200-SCS, manufactured by KEITHLEY Co., Ltd.) when a voltage of 0 MV/cm to 1.5 MV/cm was applied.

Figure 25:
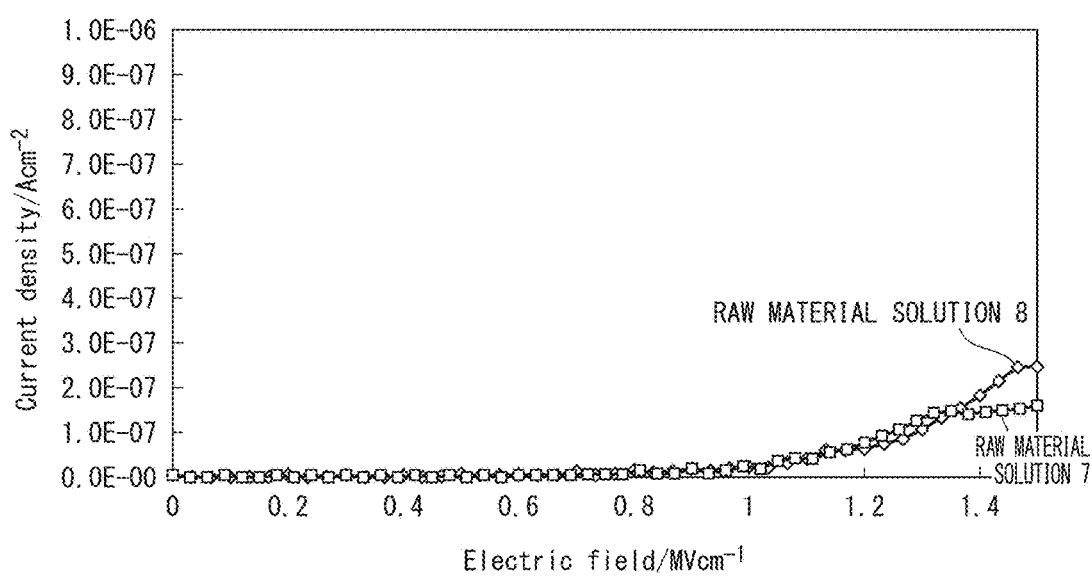
FIG. 25 is a graph showing the evaluation results of insulating properties of the insulator layer of Example 4.

FIG. 25 is a graph showing the evaluation results of insulating characteristics of the insulator layer of the fabricated sandwich cell in Example 4. The graph of FIG. 25 corresponds to the graph of FIG. 15.

As the result of measurement, it was found that the insulator layer fabricated using any of the raw material solutions 7 and 8 also had high insulating properties.

From the above results, it was found that, when the raw material solution contained tris(4-hydroxyphenyl)methane triglycidyl ether as the third organic compound, it is possible to soften the insulator layer without deteriorating coatability, dielectric constant and insulating properties.

Further, in Example 4, the insulator layer is made into a film at 105° C. or lower, which is lower than the glass transition temperature (110° C.) of PET. Therefore, it was found that, even when PET is used as the formation material of a substrate, it is possible to manufacture a laminate at a temperature at which the deformation of the substrate is less likely to occur.

Example 5

In Example 5, an organic thin film transistor was manufactured using materials in common with Example 3, except that the raw material solution 8 used in Example 4 was used as the formation material of an insulator layer.

(Fabrication of Gate Electrode)

The surface of a PET substrate was cleaned with atmospheric-pressure oxygen plasma, and then a liquid product containing the amine-based silane coupling agent having the same composition as that in Example 3 was applied onto the PET substrate by dip coating film formation (lifting speed: 1 mm/s). Thereafter, the PET substrate coated with the liquid product was heated at 105° C. for 10 minutes, so as to form a base film.

Next, 1,1,1,3,3,3-hexamethyldisilazane (HMDS, manufactured by Kanto Chemical Co., Inc.) was formed into a film by dip coating (lifting speed: 1 mm/s), and was heat-treated at 105° C. for 10 minutes.

Next, a resist material was formed into a film by dip coating (lifting speed: 1 mm/s), and was heated (prebaked) at 105° C. for 5 minutes, so as to form a resist layer.

Next, the resist layer was exposed with ultraviolet of intensity of 25 mW/cm$^2$ through a photomask for 5 seconds, heated (post-baked) at 105° C. for 5 minutes, and then immersed into 2.38 mass % of an aqueous TMAH solution for 1.5 minutes to thereby develop a mask pattern on the resist layer, so as to form an opening.

Next, a gate electrode was fabricated in the opening in the same manner as in Example 3.

Figure 26:
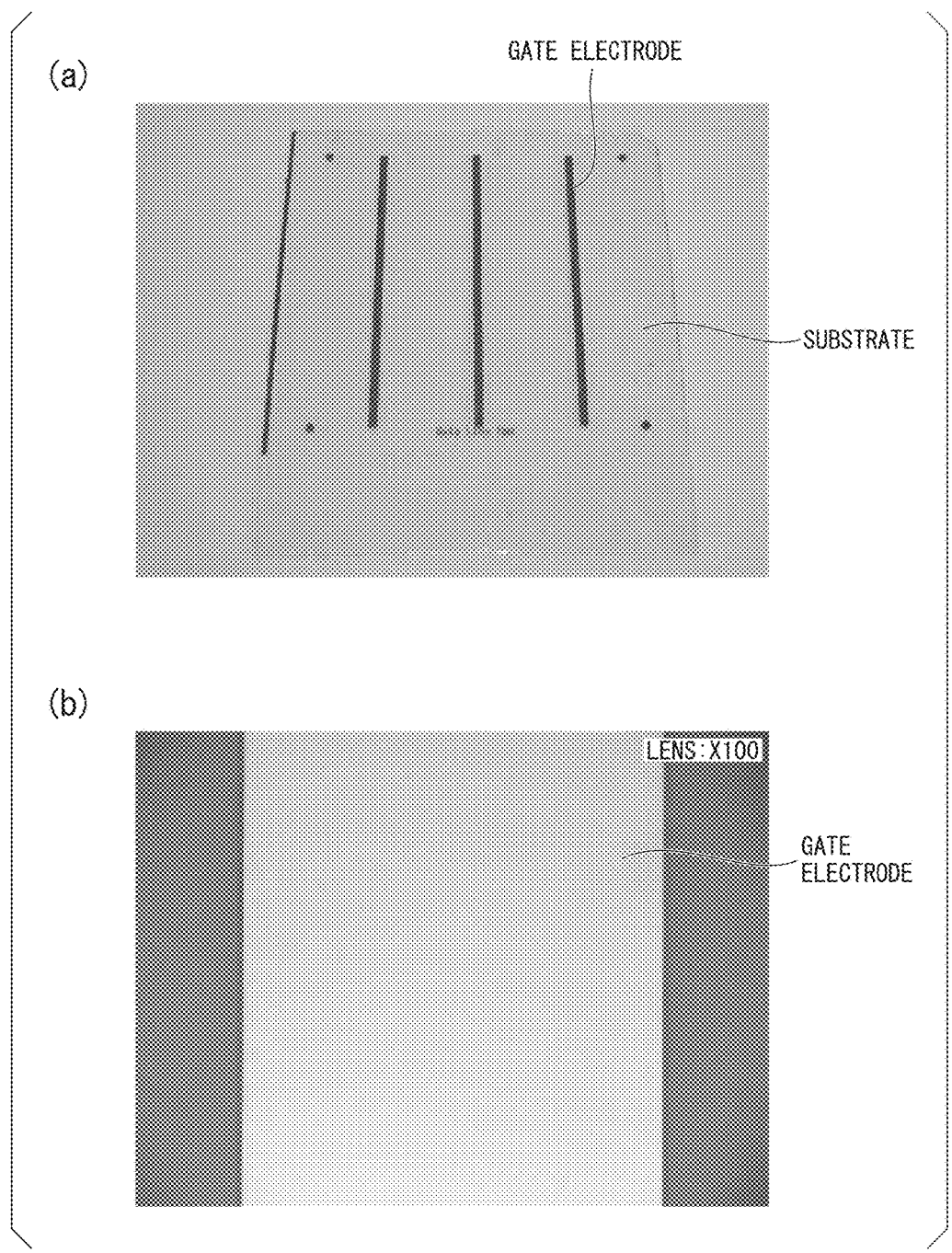
FIG. 26 shows photographs showing the results of Example 5.

FIG. 26 shows the photographs of the gate electrode. The photographs of FIG. 26 correspond to those of FIG. 19. FIG. 26 (a) is an overall photograph of the substrate provided with the gate electrode. FIG. 26 (b) is an enlarged photograph of the gate electrode using an optical microscope. From FIG. 26, it is found that a slightly uneven flat gate electrode is formed.

(Fabrication of Insulator Layer)

The surface of the gate electrode was degreased using an aqueous NaOH solution of 50 g/L and then heated at 105° C. for 10 minutes to be dried, and the surface of the substrate provided with the gate electrode was plasma-treated with atmospheric-pressure oxygen plasma.

Thereafter, the raw material solution 8 of Example 4 was applied onto the plasma-treated surface of the substrate by dip coating film formation (lifting speed: 1 mm/s). Then, the resulting product was heated at 105° C. for 10 minutes to volatilize cyclohexanone (solvent), so as to form a coating film of a curable composition.

Next, the coating film was irradiated with ultraviolet for 40 seconds through a mask having an opening in the portion forming an insulator layer. In order to accelerate curing, the ultraviolet-irradiated coating film was heated at 105° C. for 60 minutes, and then immersed into acetone for 1 minute to form a patterned film. Then, the patterned film was heat-treated at 105° C. for 30 minutes to form an insulator layer.

Figure 27:
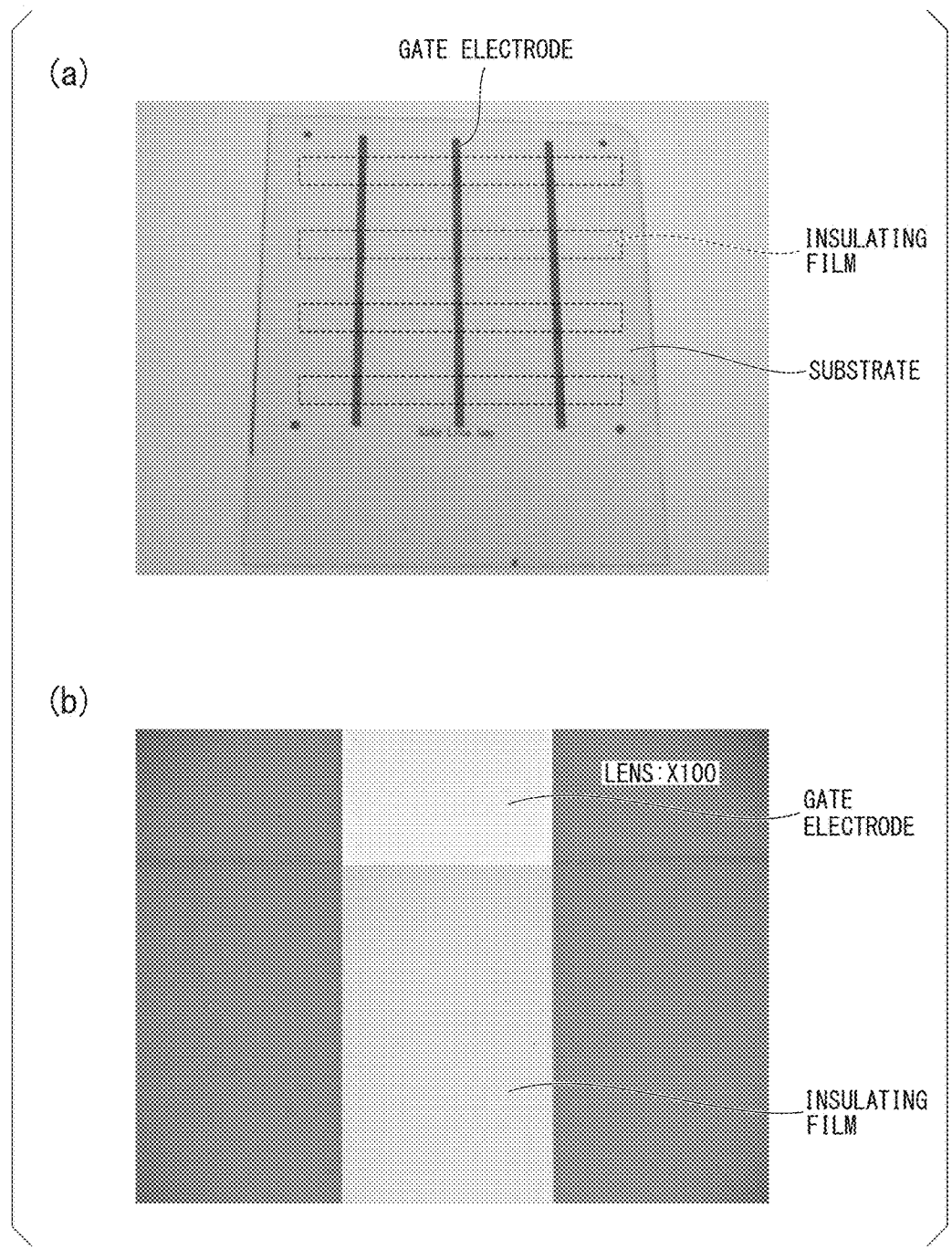
FIG. 27 shows photographs showing the results of Example 5.

FIG. 27 shows the photographs of the insulator layer. The photographs of FIG. 27 correspond to those of FIG. 20. FIG. 27 (a) is an overall photograph of the substrate provided with the insulator layer. FIG. 27 (b) is an enlarged photograph of the insulator layer. As the results of observation, coating unevenness did not occur on the surface of the insulator layer using the raw material solution 8, and an insulator layer having a flat surface was formed.

(Fabrication of Source and Drain Electrodes)

Figure 28:
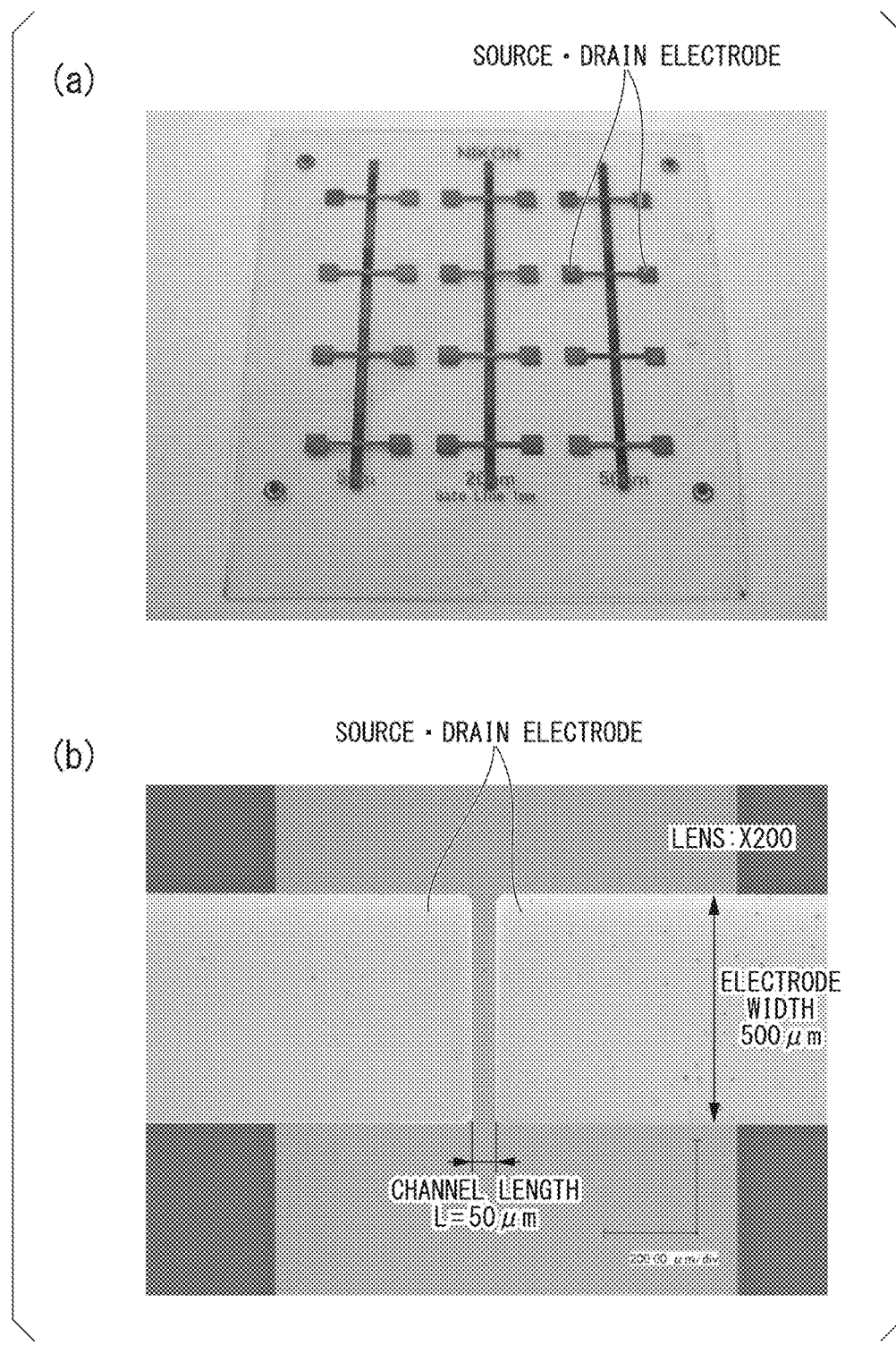
FIG. 28 shows photographs showing the results of Example 5.

Next, a source electrode and a drain electrode were fabricated in the same manner as in Example 3. FIG. 28 shows the photographs of the source electrode and the drain electrode. The photographs of FIG. 28 correspond to those of FIG. 21. FIG. 28 (*a*) is an overall photograph of the substrate provided with the source electrode and the drain electrode. FIG. 28 (*b*) is an enlarged photograph of the source electrode and the drain electrode formed on the insulator layer.

As the results of observation, in the surface of the insulator layer, it was confirmed that a good source electrode and a good drain electrode were formed. Further, damage to the insulator layer in the electroless plating process was not confirmed.

(Fabrication of Organic Semiconductor Layer)

Figure 29:
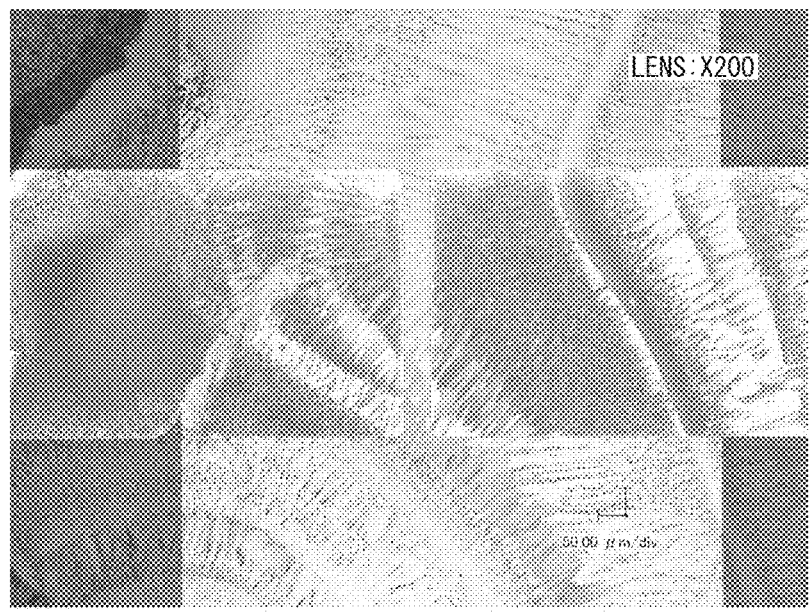
FIG. 29 is a photograph showing the results of Example 5.

Next, a semiconductor layer was formed in the same manner as in Example 3, and a transistor was fabricated. FIG. 29 is an enlarged photograph of the source electrode and the drain electrode having a surface provided with the organic semiconductor layer. The photograph of FIG. 29 corresponds to that of FIG. 22. As shown in FIG. 29, it was observed that crystals of TIPS pentacene were formed between the source electrode and the drain electrode.

(Evaluation of Transistor)

Figure 30:
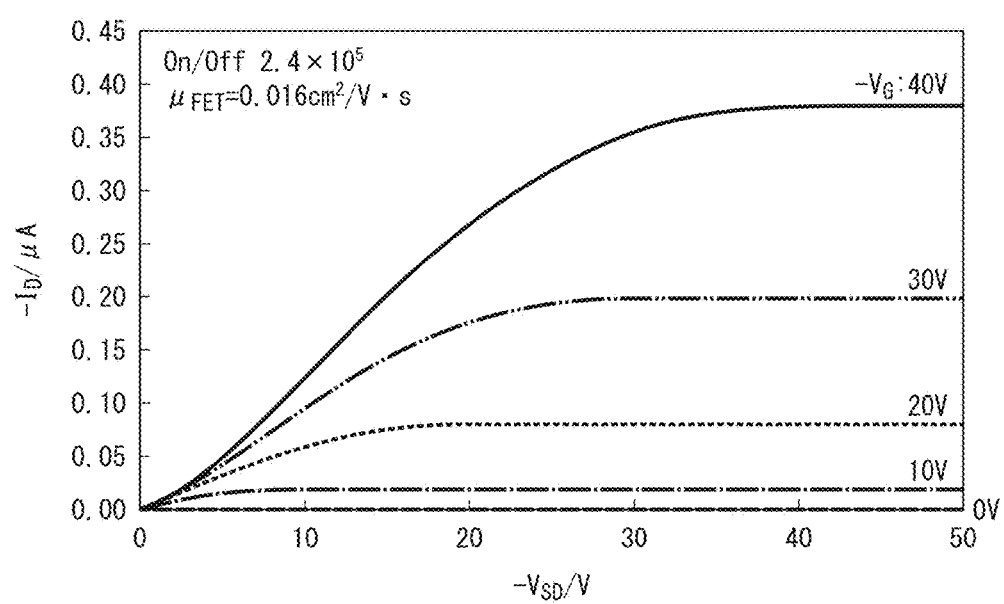
FIG. 30 is a graph showing the results of Example 5.

The transistor characteristics of the fabricated transistor were evaluated in the same manner as in Example 3. FIG. 30 is a graph showing the transistor characteristics of the transistor fabricated in Example 5. The graph of FIG. 30 corresponds to that of FIG. 23. As the result of measurement, as shown in FIG. 30, holes are induced in the channel region (between source and drain) of a semiconductor layer, and the fabricated transistor was operated as a p-type transistor.

From the above results, it was found that, when the curable composition of the present invention was used, it was possible to fabricate a transistor (organic thin film transistor) including an insulator layer having both excellent insulating properties and excellent dielectric properties in an all wet process. Further, it was found that, when the base film was formed using a silane coupling agent (primary amine), the treatment using an accelerator was not required, and the operation of electroless plating was simplified. Further, it was found that, since the base film formed using a silane coupling agent was a flat film having very small unevenness, at the time of forming a laminated structure, uneven shape was not imparted to the configuration of the upper layer of the base film, and it was possible to fabricate a high-performance transistor. Moreover, it was found that, since it was possible to coat the entire surface of source and drain electrodes with a metal material having a work function that provides a small energy gap with HOMO of the formation material of the organic semiconductor layer by using an electroless plating method, it was possible to provide a transistor having small electrical contact resistance between the organic semiconductor layer and the source and drain electrodes.

From the above results, the usefulness of the present invention has been confirmed.

What is claimed is:

1. A method of manufacturing a transistor, comprising:
   forming a gate electrode on a substrate;
   applying a solution containing the composition comprising (a) a first organic compound represented by Formula (1) below,
   (b) a second organic compound represented by Formula (2) below, and
   (c) a photocationic polymerization initiator

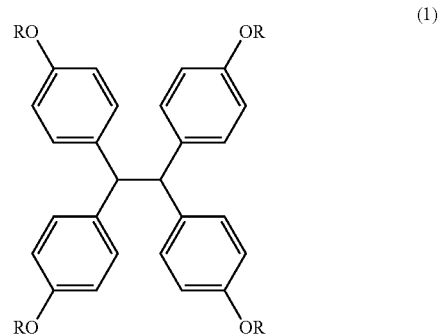

(R represents a hydrogen atom or a glycidyl group, a plurality of Rs may be identical to or different from each other, but each of at least two Rs is a glycidyl group),

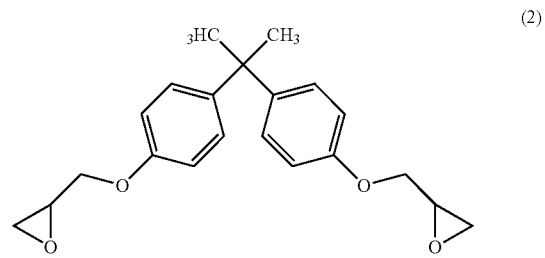

over the gate electrode to form a coating film;
irradiating the coating film with light containing light having an absorption wavelength of the photocationic polymerization initiator contained in the coating film to form a latent image in the light-irradiated region of the coating film;
developing the coating film to form an insulator layer; and
forming a source electrode and a drain electrode on the surface of a layer including the insulator layer.

2. The method of manufacturing a transistor according to claim 1, wherein the coating film is selectively irradiated with the light.

3. The method of manufacturing a transistor according to claim 1, wherein at least one of the gate electrode, the source electrode, and the drain electrode is formed by:
   applying a formation material containing a silane coupling agent having a group capable of capturing a metal, which is an electroless plating catalyst, to form a base film; and
   capturing the metal on the surface of the base film and then performing electroless plating.

4. The method of manufacturing a transistor according to claim 3, wherein the source electrode and the drain electrode are formed by:
   forming a source base film and a drain base film, each being the base film; and
   then capturing the metal on the surface of each of the source base film and the drain base film to perform electroless plating.

5. The method of manufacturing a transistor according to claim 4, wherein the source base film and the drain base film are formed as a continuous film.

6. The method of manufacturing a transistor according to claim 3,
wherein the gate electrode is formed by:
forming a gate base film, which is the base film; and
then capturing the metal on the surface of the gate base film to perform electroless plating.

7. The method of manufacturing a transistor according to claim 3, wherein the silane coupling agent has an amino group.

8. The method of manufacturing a transistor according to claim 7, wherein the silane coupling agent is a primary amine or a secondary amine.

9. The method of manufacturing a transistor according to claim 3, wherein the layer including the insulator layer includes: the insulator layer; and an organic semiconductor layer disposed on the insulator layer and having a surface on which the source electrode and the drain electrode are formed.

10. The method of manufacturing a transistor according to claim 3, comprising:
forming the source electrode and the drain electrode; and then forming an organic semiconductor layer that is in contact with surfaces of the source electrode and the drain electrode that face each other.

11. The method of manufacturing a transistor according to claim 9, comprising, prior to forming the source electrode and the drain electrode:
forming a resist layer having an opening corresponding to the source electrode and the drain electrode and capturing the metal on the surface of the base film formed on the surface exposed at least in the opening;
performing first electroless plating and then removing the resist layer; and
performing second electroless plating on the surface of an electrode formed by the first electroless plating to form the source electrode and the drain electrode,
wherein the energy level difference between the work function of a metal material used in the second electroless plating and the energy level of a molecular orbital used for electron transfer in a formation material of the organic semiconductor layer is smaller than the energy level difference between the work function of a metal material used in the first electroless plating and the energy level of the molecular orbital.

12. The method of manufacturing a transistor according to claim 1, wherein the substrate is made of a non-metallic material.

13. The method of manufacturing a transistor according to claim 12, wherein the substrate is made of a resin material.

14. The method of manufacturing a transistor according to claim 13, wherein the substrate has flexibility.

* * * * *

UNITED STATES PATENT AND TRADEMARK OFFICE
CERTIFICATE OF CORRECTION

PATENT NO. : 10,074,803 B2
APPLICATION NO. : 15/495360
DATED : September 11, 2018
INVENTOR(S) : Shohei Koizumi et al.

Page 1 of 1

It is certified that error appears in the above-identified patent and that said Letters Patent is hereby corrected as shown below:

On the Title Page
Item [60] (Related U.S. Application Data), delete "and" and insert -- which is --, therefore.

In the Specification
Column 1, Line 9, delete "divisonal" and insert -- divisional --, therefore.

Signed and Sealed this
Sixth Day of November, 2018

Andrei Iancu
*Director of the United States Patent and Trademark Office*